(12) United States Patent
Ley et al.

(10) Patent No.: US 8,852,664 B2
(45) Date of Patent: Oct. 7, 2014

(54) NEO-MENTHYL DERIVATIVES AS FLAVOR MATERIALS

(75) Inventors: Jakob Peter Ley, Holzminden (DE);
Heiko Oertling, Holzminden (DE);
Michael Backes, Holzminden (DE);
Tobias Vössing, Beverungen (DE)

(73) Assignee: Symrise AG, Holzminden (DE)

( * ) Notice: Subject to any disclaimer, the term of this patent is extended or adjusted under 35 U.S.C. 154(b) by 682 days.

(21) Appl. No.: 12/482,210

(22) Filed: Jun. 10, 2009

(65) Prior Publication Data

US 2009/0311401 A1    Dec. 17, 2009

Related U.S. Application Data

(60) Provisional application No. 61/061,273, filed on Jun. 13, 2008.

(51) Int. Cl.

| | | |
|---|---|---|
| A23L 1/228 | (2006.01) | |
| A23L 1/226 | (2006.01) | |
| C07C 335/14 | (2006.01) | |
| A23L 1/22 | (2006.01) | |
| C07C 271/36 | (2006.01) | |
| C07C 271/34 | (2006.01) | |
| C07C 271/38 | (2006.01) | |
| C07C 275/26 | (2006.01) | |

(52) U.S. Cl.
CPC ......... *A23L 1/22091* (2013.01); *A23L 1/22642* (2013.01); *C07C 335/14* (2013.01); *A23L 1/226* (2013.01); *C07C 271/36* (2013.01); *C07C 271/34* (2013.01); *C07C 2101/02* (2013.01); *C07C 271/38* (2013.01); *C07C 2101/14* (2013.01); *C07C 2101/08* (2013.01); *C07C 275/26* (2013.01); *A23L 1/22628* (2013.01)
USPC .......................................... 426/538; 426/534

(58) Field of Classification Search
USPC ....................................................... 426/534
See application file for complete search history.

(56) References Cited

U.S. PATENT DOCUMENTS

| | | | |
|---|---|---|---|
| 3,159,585 A | 12/1964 | Evans et al. | |
| 3,971,852 A | 7/1976 | Brenner et al. | |

(Continued)

FOREIGN PATENT DOCUMENTS

| | | |
|---|---|---|
| DE | 4226043 | 2/1994 |
| EP | 242325 | 10/1987 |

(Continued)

OTHER PUBLICATIONS

Leffingwell, J.C., Shackelford, R.E. 1974. "Laevo-menthol syntheses and organoleptic properties." Cosmetics and Perfumery. vol. 89. pp. 69-72, 74, 76, 78.*

(Continued)

*Primary Examiner* — Nikki H Dees
(74) *Attorney, Agent, or Firm* — Novak Druce Connolly Bove + Quigg LLP

(57) ABSTRACT

The present invention relates primarily to the use of particular ureas, thioureas, carbamates, thiocarbamates and guanidines based on the neomenthyl structure and corresponding mixtures with one another or with further compounds as flavor materials or flavor material mixtures for producing, imparting, modifying and/or enhancing savory flavor notes. the invention furthermore relates to particular compositions, preparations and semifinished products which comprise the said compounds, as well as methods for producing, imparting, modifying and/or enhancing particular flavor impressions. Lastly, the invention also relates to the compounds themselves and to corresponding mixtures.

17 Claims, 3 Drawing Sheets

(56) References Cited

U.S. PATENT DOCUMENTS

| | | | |
|---|---|---|---|
| 4,518,615 A | 5/1985 | Cherukuri et al. | |
| 4,532,145 A | 7/1985 | Saleeb et al. | |
| 5,093,136 A | 3/1992 | Panhorst et al. | |
| 5,124,162 A | 6/1992 | Boskovic et al. | |
| 5,266,336 A | 11/1993 | McGrew et al. | |
| 5,601,858 A | 2/1997 | Mansukhani et al. | |
| 5,703,123 A * | 12/1997 | Pelzer et al. | 514/512 |
| 5,955,496 A | 9/1999 | Hammock et al. | |
| 6,531,506 B1 | 3/2003 | Kroetz et al. | |
| 6,986,709 B2 | 1/2006 | Hughs-Baird et al. | |
| 2005/0084506 A1 | 4/2005 | Tachdjian et al. | |
| 2006/0063764 A1* | 3/2006 | Gautschi | 514/237.5 |
| 2007/0134389 A1 | 6/2007 | Pei et al. | |

FOREIGN PATENT DOCUMENTS

| | | |
|---|---|---|
| EP | 1284145 | 2/2003 |
| EP | 1803357 | 7/2007 |
| EP | 1989944 A1 | 11/2008 |
| EP | 2064959 A1 | 6/2009 |
| WO | WO-2004000023 | 12/2003 |
| WO | WO-2004000787 | 12/2003 |
| WO | WO-2004043906 | 5/2004 |
| WO | WO-2004078302 | 9/2004 |
| WO | WO-2005020897 | 3/2005 |
| WO | WO-2005096841 | 10/2005 |
| WO | WO-2006024587 | 3/2006 |
| WO | WO-2006058893 | 6/2006 |
| WO | WO-2006106023 | 10/2006 |
| WO | WO-2006127738 | 11/2006 |
| WO | WO-2006127740 | 11/2006 |
| WO | WO-2007003527 | 1/2007 |
| WO | WO-2007014879 | 2/2007 |
| WO | WO-2007107596 | 9/2007 |

OTHER PUBLICATIONS

A. Woidich, et al., "The Use of N-Alkylcarbamates in Sample Mapping of Terpene Alcohols," *Mikrochimica Acta*, vol. 3, Nos. 1-2, pp. 117-124, 1989.
P. Jumaryatno et al., "Isocyanates in marine sponges: Axisocyanate-3, a new sesquiterpene from *Acanthella cavernosa*," *ARKIVOC*, vol. 7, pp. 157-166, 2007.
B. Peng, et al., "Chiral guanidine catalyzed Michael addition reaction and DielsAlder reaction of anthrone and N-methylmaleimide," *Chinese Journal of Chemistry*, vol. 18, No. 3, pp. 411-413, 2000.
V. Benecke et al., "Isocyanate als universelle Reagentien bei der Derivatbildung fur die gaschromatographische Enantiomerentrennung," *Angew. Chem.*, vol. 94, No. 9, pp. 709-710, 1982.
J. Izdebski, et al., "Application of New Carbodiimides to Peptide Synthesis," 20th *Peptides Proc. Eur. Pept. Symp.*, pp. 16-18, 1989.
A. Macbeth, et al., "The Influence of Configuration on teh Thermal Stability of N-Menthylphthalamic Acids.," *Journal Chemical Soc.*, pp. 2968-2972, 1951.
J. Read, et al., "Researches in the Menthone Series. Part II. Optically Active Menthones and Methylamines.," *Journal Chemical Soc.*, pp. 2209-2223, 1926.
J. Read, et al., "Researches in the Menthone Series. Part III. Optically Inactive Menthylamines.," *Journal Chemical Soc.*, pp. 2223-2234, 1926.
M. Forster et al., "CXLIX.-Dihydrocinnamenylcarbimide (β-Phenylethyl iso Cyanate)," *Journal of the Chemical Society, Transactions*, vol. XCIX., Part II, pp. 1337-1340, 1911.
Gastambide, Par B., "Empêchement Stérique et Chromatographie", *Ann. de Chim.*, No. 9, pp. 257-309, 1954.
Von K., "Ueber die Bestimmung der Konfiguration raumisomerer hydroaromatischer Verbindungen", *Sitzb. Ges. Beforderung gesamten Naturwissenschaften Marburg*, vol. 62 (4), pp. 113-135.
V. Niebergall, et al., "Untersuchungen über das Verhalten von Cyclohexylisocyanat gegenüber Lebensmitteln bei der Migration*)",*Deutsche Lebensmittel-Rundschau*, vol. 80 (6), pp. 170-174, 1984.
W.E.Pereira, et al., "Electron-Impact Promoted Fragmentation of Alkyl-N-(1-Phenylethyl)-Carbamates of Primary, Secondary and Tertiary Alcohols", *Organic Mass Spectrometry*, vol. 5 (2), pp. 157-169, 1971.
MM. R. Vieillefosse, et al., "Nouveaux anesthésiques loxaux dans la série des uréthanes cyclaniques", *Annales Pharmaceutiques Francaises*, 16, pp. 408-413, 1958.
A. Ghosh, et al., "Di(2-Pyridyl) Carbonate Promoted Alkoxycarbonylation of Amines: A Convenient Synthesis of Functionalized Carbamates", *Tetrahedron Letters*, vol. 32, No. 34, pp. 4251-4254, 1991.
K. Bauer, et al., "Common Fragrance and Flavor Materials", Wiley-VCH, 4$^{th}$. Ed., Weinheim 2001 (excerpts).
Von O. Wallach, Zur Kenntiness der Terpene und der ätherischen Oele, Ann. Chem., 276, pp. 296-313, 1893.
T. Nambara, et al., "High Pressure Liquid Chromatographic Resolution of Amino Acid Enantiomers by Derivatization with New Chiral Reagents", *Anal. Chim. Acta*, vol. 101 (1), pp. 111-116, 1978.
D. Ma, et al., "Enantioselective synthesis of functionalized α-amino acids via a chiral guanidine catalyzed Michael addition reaction," *Tetrahedron:Asymmetry*, vol. 10 (4), pp. 713-719, 1999.
Read J; Roebuck D: "The different reaction velocities of enantiomer with a commonoptically active reagent. part II. Reactions between stereoisomeric menthols and menthyl isocyatates", Journal of the Chemical Society, Chemical Society, Letchworth., GB, Jan. 1, 1952, Seiten 812-816, XP009122846.
Howson Pickard and William Oswald Littlebury R: "Alcohols of the hydroaromatic and terpene series. Part I. The mentols corresponding with optically inactive menthone," Journal of the Chemical Society, Chemical Society, Letchworth., GB, Bd. 101, Jan. 1, 1912, Seiten 109-127, XP009122803.
Bernard Gastambide: "Empêchement stérique et chromatographie" Annales De Chimie, Masson, Paris, FR, Bd 12, Jan. 1, 1954, Seiten 257-305, XP009122801.
Ma D; Cheng K: "Enantioselective synthesis of functionalized alpha-amino acids via a chiral guanidine catalyzed Michael addition reaction," Tetrahedron:Asymmetry, Pergamon Press Ltd, Oxford, GB, Bd. 10, Nr. 4, Feb. 26, 1999, Seiten 713-719, XP004222844.
Wallach O; Werner D F: "Zur Kenntniss der Terpene und der ätherischen Oele", Justus Liebigs Annalen Der Chemie, Verlag Chemie GmbH, Weinheim,; DE, Jan. 1, 1898, Seiten 278-285, XP009122804.
Chinese Office Action, Chinese Application No. 200910148323.4, dated May 14, 2012.
Official Notification for Patent Registration Formalities / Official Notification on Grant of Patent Right for Invention with English translation, issued in parallel Chinese Application No. 200910148323.4.

* cited by examiner

NEO-MENTHYL DERIVATIVES AS FLAVOR MATERIALS

CROSS-REFERENCE TO RELATED APPLICATION

This application claims benefit of priority to U.S. Provisional Application No. 61/061,273, filed on Jun. 13, 2008, which is incorporated herein by reference in its entirety.

The present invention relates primarily to the use of particular compounds based on the neo-menthyl structure (in particular derivatives of urea, thiourea, and carbamates, thiocarbamates and guanidines) of the formulae (I) and (ent-I) (see below) and corresponding mixtures with one another or with further compounds as flavor materials or flavor material mixtures. The compounds to be used according to the invention are suitable in particular for producing, imparting, modifying and/or enhancing savory flavor notes, in particular an umami flavor or saltiness. The invention furthermore relates to particular compositions, preparations and semifinished products which comprise an effective flavoring amount of the said compounds of formulae (I) and (ent-I) and to particular methods for producing, imparting, modifying and/or enhancing particular flavor impressions, in particular umami and saltiness. Lastly, the invention also relates to novel compounds of the formulae (I) and (ent-I) which impart particular flavor impressions, and to corresponding mixtures.

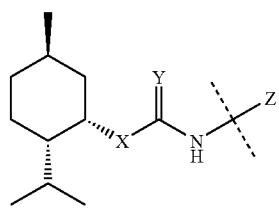
(I)

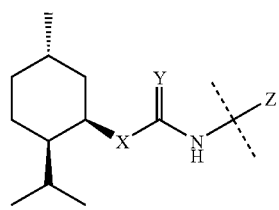
(ent-I)

Further aspect may be found in the following description, the exemplary embodiments, the figure and the claims.

Various D/L-menthyl carbamates have been known for a long time as cooling agents. For instance, DE4226043 describes the use of the following derivatives as agents with a cooling effect, without more accurate description of the stereochemistry:

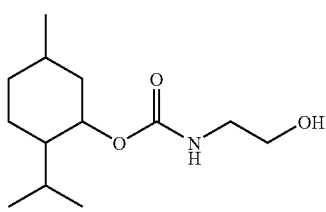

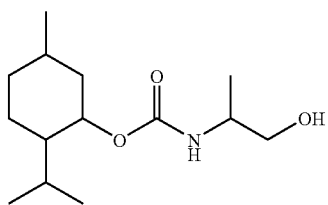

The flavorlessness of the compounds and the measured rotation value suggest the use of (L)-menthol as the starting material.

Documents WO 2006/127738 and WO 2006/127740 describe the use of the tert-butyl derivative of the D/L-menthol series as a cooling agent for use in chewing gum.

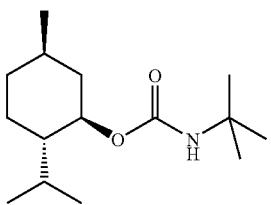 [SMILES: CC(C)[C@@H]1CC[C@@H](C)C[C@H]1OC(=O)NC(C)(C)C]

EP1284145 proposes aromatic carboxylic acid derivatives of the general formula

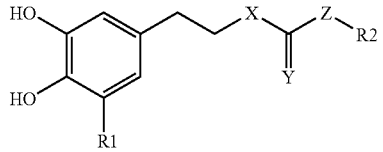

where X, Y and Z independently of one another denote O, S and NH. These compounds may be employed as radical traps, in which case R2 may also contain an (L)-menthyl residue. The flavor of the compounds, however, was not studied further.

The publication WO 2005/020897 discloses various carbamates and ureas based on a menthyl structure, which can be used as Trp-r8 modulators, as well as compositions, including pharmaceutical compositions, which contain one of these compounds and pharmaceutically usable auxiliaries, excipients and diluents. The structure of some compounds disclosed in WO 2005/020897 corresponds to the following formulae:

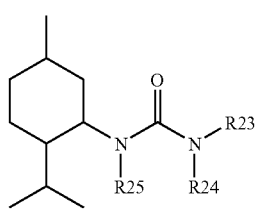
VIII-C

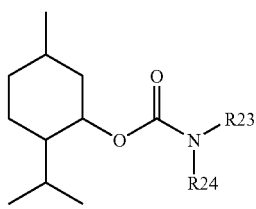

VIII-D

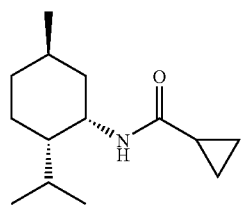

FEMA 4558

For the substituents R23, R24 and R25, to this extent an extensive list of possible mutually independent meanings is respectively disclosed. The examples shown each contain a (−)-menthyl- or (−)-menthylamine basic structure. The flavor of the compounds is not described.

Furthermore, EP 1 803 357 describes that carbamates of the general formula

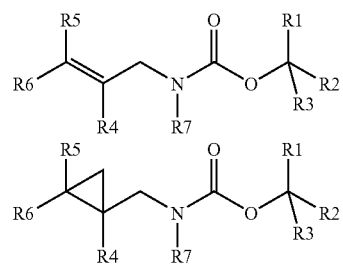

have flavor-modifying properties which can be used in particular to enhance an umami impression and to enhance saltiness. Some examples are also presented in which —CR1R2R3=menthyl (without more accurate definition of the stereochemistry).

Claim 60 of the publication US 2005/0084506 describes numerous non-natural compounds of the general structural formula

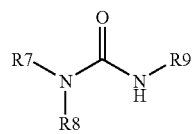

for the modification of flavor, in particular the sweet and savory properties. For the substituents R7, R8 and R9, to this extent an extensive list of possible mutually independent meanings is respectively disclosed. The menthyl basic structure is not however explicitly described as a possible substituent, and the focus of this part of the publication is on heteroaromatic substituents.

The U.S. Provisional Applications 60/916,589 of May 8, 2007 (Symrise) and 60/984,023 of Oct. 31, 2007 (Symrise) both described that the relative stereochemistry of the menthyl structure can have an essential effect on the flavor properties of the corresponding compounds. In this case, the relative neo-stereochemistry of the menthyl basic structure is important for enhancing a savory and/or salty flavor impression of these compounds, of which racemic neo-menthyl cyclopropanecarboxamide (FEMA 4558) already has GRAS status.

There is a constant need to find new flavor and aroma materials, i.e. actively flavoring compounds or compounds which can produce, impart, modify or enhance a savory flavor impression. In particular, there is a need for such compounds which can produce, impart, modify or enhance the "umami" flavor impression. In view of the increased health awareness on the part of consumers, compounds which can produce, impart, modify or enhance saltiness are also being sought. For preferred applications in the savory field, the compounds to be provided should ideally produce, impart, modify or enhance both the "umami" flavor impression and saltiness.

It was therefore an object of the present invention to provide methods and compounds by means of which desired flavor notes (preferably the directions "umami" and/or salty) can be produced, imparted, modified or enhanced.

This object is achieved according to the invention by the use of a compound or a mixture consisting of two or more compounds or containing one or more compounds selected from the group consisting of compounds of the formulae (I) and (ent-I)

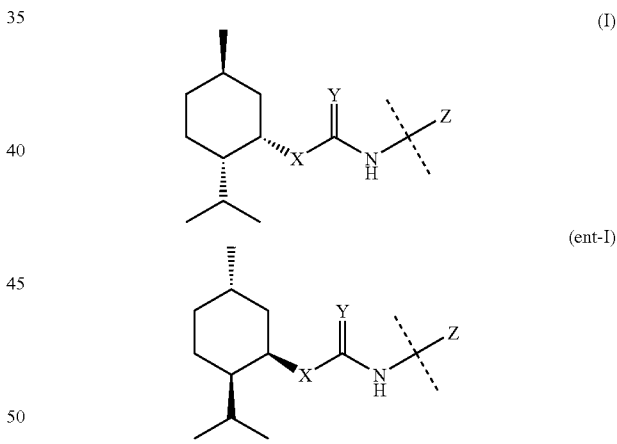

wherein the dashed line respectively marks the bond which links the organic residue Z to the neighboring nitrogen atom in formula (I) or (ent-I), and wherein the following apply independently of one another in the formulae (I) and (ent-I):

X=NH or O;

Y=O, S or NR1, where R1 denotes hydrogen, methyl, ethyl, propyl or isopropyl; and Z=organic residue having at most 15 C atoms, as a flavor material or flavor material mixture.

The use of a compound or a mixture as defined above as a flavor material or flavor material mixture is preferred when the following applies for the compound of formulae (I) and (ent-I) or for one or more or all compounds of the formulae (I) and (ent-I) in the mixture:

the sum of the number of carbon and oxygen atoms in the organic residue Z is at most 15 and the number of oxygen atoms is at most 4, and the atom by which the organic residue Z is bound to the neighboring nitrogen in formula (I) or (ent-I) is carbon, with the condition that the organic residue Z does not contain a C—C double or triple bond, contains at most one aromatic ring, and is not a group —C(=Y²)—R2 in which Y² has any of the meanings specified above for Y and R2 is any organic residue.

Preferably, and this applies for all the configurations above and below, Z is an organic residue consisting of carbon and hydrogen atoms as well as optionally oxygen atoms.

The use of compounds of the following type is not preferred, in which Z is a group —C(=Y²)—R2 where R2 represents any organic residue and that stated above applies for X, Y and Y².

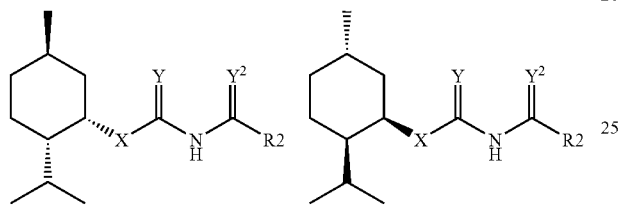

The use of a compound or a mixture as defined above as a flavor material or flavor material mixture is preferred in particular when the following applies (i) for the compound of formula (I) or (ent-I) or (ii) for one or more or all compounds of the formulae (I) and (ent-I) in the mixture:

Y=O or S and the sum of the number of carbon and oxygen atoms in the organic residue Z is at most 11 and the number of oxygen atoms is at most 2.

The use of a compound or a mixture as defined above as a flavor material or flavor material mixture is particularly preferred when the following apply (i) for the compound of formula (I) or (ent-I) or (ii) for one or more or all compounds of the formulae (I) and (ent-I) in the mixture:

X=NH or O.

Y=O.

Z=organic residue in which the sum of the number of carbon and oxygen atoms is at most 11 and the number of oxygen atoms is at most 2, and the atom by which the organic residue Z is bound to the neighboring nitrogen in formula (I) or (ent-I) is carbon, with the condition that the organic residue Z does not contain a C—C double or triple bond, contains at most one aromatic ring, and is not a group —C(=Y²)—R2 in which Y² has any of the meanings specified above for Y and R2 is any organic residue.

The use of a compound or a mixture as defined above is also preferred when the following applies for the compound of formulae (I) and (ent-I) or for one or more or all compounds of the formulae (I) and (ent-I) in the mixture:

Y=O; and

Z=organic residue in which the sum of the number of carbon and oxygen atoms is at most 11 and the number of oxygen atoms is at most 2, where Z is a residue selected from the group consisting of optionally singly or multiply substituted alkyl, $C_3$-$C_7$ cycloalkyl, phenyl and phenylalkyl, one or more substituents optionally present in the residue Z being selected from the group consisting of OH, $C_1$-$C_4$ alkoxy, $C_1$-$C_4$ alkoxycarbonyl and cyclic ether, in which case cyclic groups in the organic residue are optionally substituted by $C_1$-$C_4$ alkyl groups.

The use of a compound or a mixture as defined above as a flavor material or flavor material mixture is preferred in particular when the organic residue Z (i) for the compound of formulae (I) or (ent-I) or (i) for one or more or all compounds of the formulae (I) and (ent-I) in the mixture is selected from the group consisting of:

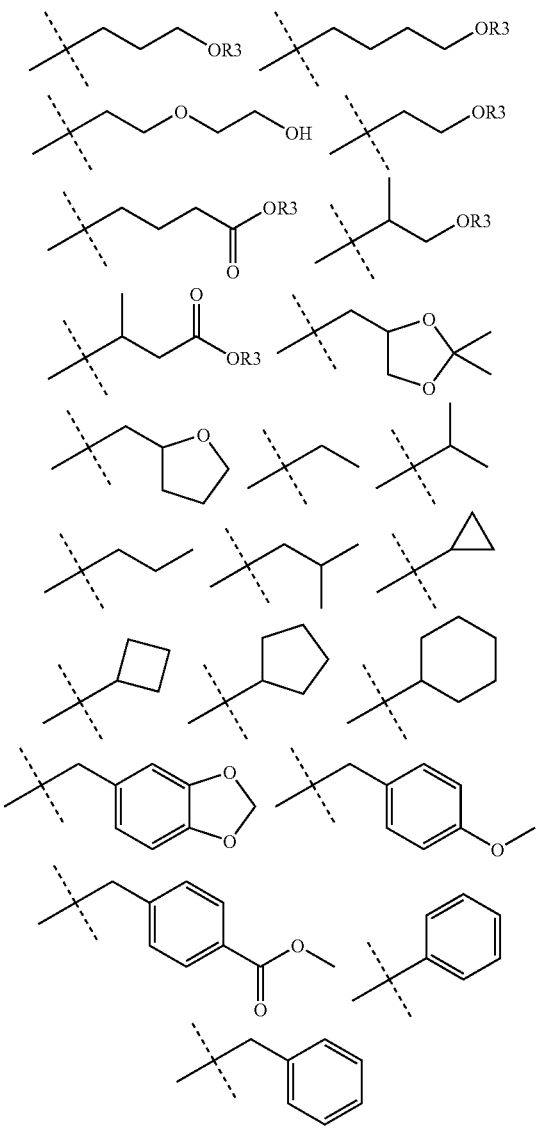

wherein optionally present residues R3 independently of one another denote hydrogen, methyl, ethyl, n-propyl, iso-propyl, n-butyl, iso-butyl and the dashed line respectively marks the bond which links the organic residue Z to the neighboring nitrogen atom in formula (I) or (ent-I).

The use of a compound or a mixture as defined above is also particularly preferred when the following apply for the compound of formulae (I) and (ent-I) or for one or more or all compounds of the formulae (I) and (ent-I) in the mixture:

Y=O; and

Z=organic residue in which the sum of the number of carbon and oxygen atoms is at most 11 and the number of oxygen atoms is at most 2, where Z is an optionally singly or multiply substituted straight-chained or branched $C_1$-$C_6$ alkyl residue, one or more optionally present substituents preferably being selected from the group consisting of OH, $C_1$-$C_4$ alkoxy and $C_1$-$C_4$ alkoxycarbonyl.

The use of a compound or a mixture as defined above is as a flavor material or flavor material mixture is more particularly preferred when (i) the compound of formula (I) and (ent-I) or (ii) one, two, more than two or all compounds of the formulae (I) and (ent-I) in the mixture are selected from the group consisting of:

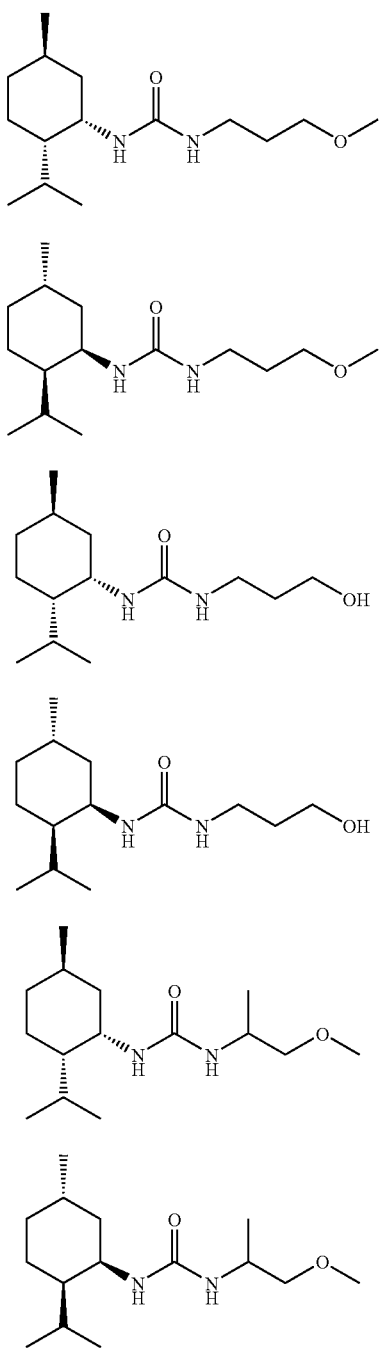

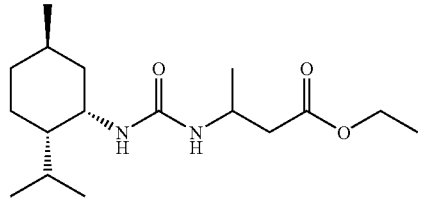

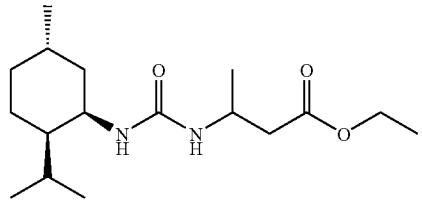

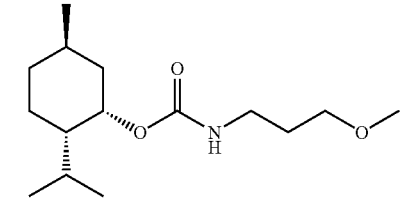

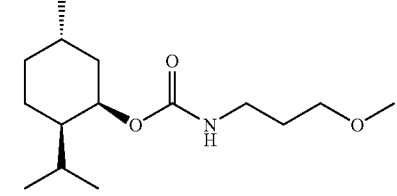

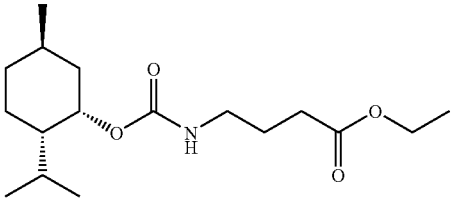

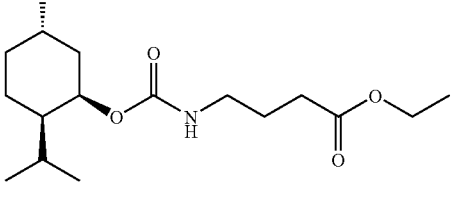

(1) 1-((1S,2S,5R)-2-isopropyl-5-methyl-cyclohexyl)-3-(3-methoxy-propyl)-urea
(2) 1-((1R,2R,5S)-2-isopropyl-5-methyl-cyclohexyl)-3-(3-methoxy-propyl)-urea
(3) 1-(3-hydroxy-propyl)-3-((1S,2S,5R)-2-isopropyl-5-methyl-cyclohexyl)-urea
(4) 1-(3-Hydroxy-propyl)-3-((1R,2R,5S)-2-isopropyl-5-methyl-cyclohexyl)-urea
(5) 1-((1S,2S,5R)-2-isopropyl-5-methyl-cyclohexyl)-3-(2-methoxy-1-methyl-ethyl)-urea
(6) 1-((1R,2R,5S)-2-isopropyl-5-methyl-cyclohexyl)-3-(2-methoxy-1-methyl-ethyl)-urea
(7) 3-[3-((1S,2S,5R)-2-isopropyl-5-methyl-cyclohexyl)-ureido]-butyric acid ethyl ester
(8) 3-[3-((1R,2R,5S)-2-isopropyl-5-methyl-cyclohexyl)-ureido]-butyric acid ethyl ester (9) (3-methoxy-propyl)-carbamic acid (1S,2S,5R)-2-isopropyl-5-methyl-cyclohexyl ester
(10) (3-methoxy-propyl)-carbamic acid (1R,2R,5S)-2-isopropyl-5-methyl-cyclohexyl ester
(11) 4-((1S,2S,5R)-2-isopropyl-5-methyl-cyclohexyloxy-carbonylamino)-butyric acid ethyl ester
(12) 4-((1R,2R,5S)-2-isopropyl-5-methyl-cyclohexyloxy-carbonylamino)-butyric acid ethyl ester The mixtures to be used according to the invention preferably contain two or more of the aforementioned particularly preferred or more particularly preferred compounds of the formulae (I) and (ent-I), or consist of two or more of the aforementioned particularly preferred or more particularly preferred compounds of the formulae (I) and (ent-I).

It is more particularly preferable to use a mixture as defined above, wherein the mixture contains one or more pairs of compounds of formulae (I) and (ent-I) or consists of one or more such pairs, each pair consisting of a compound of the formula (I) and a compound of the formula (ent-I) as defined above (and preferably referred to as preferred),
wherein
the meanings of X and Y in the compound of formula (I) are respectively identical to the meanings of X and Y in the compound of formula (ent-I) and
wherein
(a) the meaning of Z in the compound of formula (I) is identical to the meaning of Z in the compound of formula (ent-I) or
(b) Z in the compound of formula (I) and Z in the compound of formula (ent-I) contain or one or more chiral centers and differ only by the absolute configuration at one, several or all of these chiral centers,
wherein each pair is preferably an enantiomer or epimer pair.

In some studies, it has been found that the compounds of formulae (I) and (ent-I) to be used according to the invention, or the mixture is described above and below can produce, impart, modify and/or enhance an umami flavor particularly well both in the initial taste (impact) and in the longer-lasting taste perception in sodium glutamate-reduced foods, sodium glutamate-free foods and in foods with a reduced sodium chloride content, for example in savory foods such as tomato soup, chicken soup, savory snacks, ready-made pizza, potato chips and popcorn.

The additional ability—similarly to monosodium glutamate—also to produce and/or enhance a perception of saltiness, leads to a pleasantly received taste experience which in many cases is even reported as preferable to sodium glutamate. Some compounds of the formulae (I) and (ent-I), or the above-described mixtures to be used according to the invention, produce, impart, modify and/or enhance the "salty" flavor impression without having a strong umami character. These are particularly suitable for use in foods containing sodium chloride, for example salt liquorice, salt sticks and crackers in order to produce, impart, modify and/or enhance the pure salt flavor while simultaneously reducing the sodium chloride content.

In comparison with other compounds tasting of umami, for example a mixture of 1-((1S,2S,5R)-2-isopropyl-5-methyl-cyclohexyl)-3-(3-methoxy-propyl)-urea (1) and 1-((1R,2R,5S)-2-isopropyl-5-methyl-cyclohexyl)-3-(3-methoxy-propyl)-urea (2) is distinguished by a clear umami flavor very closely approximating sodium glutamate (MSG), which also significantly enhances the saltiness of the base but without tasting unpleasantly sweet. This is also shown by the spider diagram appended as FIG. 1, in which an American beef extract as a base is compared with (i) such a base having 1 ppm of a 1:1 mixture of 1-((1S,2S,5R)-2-isopropyl-5-methyl-cyclohexyl)-3-(3-methoxy-propyl)-urea (1) and 1-((1R,2R,5S)-2-isopropyl-5-methyl-cyclohexyl)-3-(3-methoxy-propyl)-urea (2) added and (ii) with such a base having 0.05 wt. % of MSG (sodium glutamate) added. The observations above apply accordingly for all mixtures to be used according to the invention.

The genuine MSG-like character is furthermore confirmed by the spider diagram appended as FIG. 2. Here, a base for a chicken aroma is compared with (i) such a base having 1 ppm of the pure-enantiomer compound 1-((1S,2S,5R)-2-isopropyl-5-methyl-cyclohexyl)-3-(3-methoxy-propyl)-urea (1) added and (ii) with such a base having 0.2 wt. % of a standard aroma (containing MSG) added.

In the spider diagram appended as FIG. 3, American beef extract as a base is compared with (i) such a base having 1 ppm of a 1:1 mixture of 3-[3-((1S,2S,5R)-2-isopropyl-5-methyl-cyclohexyl)-ureido]-butyric acid ethyl ester (7) and 3-[3-((1R,2R,5S)-2-isopropyl-5-methyl-cyclohexyl)-ureido]-butyric acid ethyl ester (8) added and (ii) with such a base having 0.05 wt. % of MSG (sodium glutamate) added.

In another test, the saltiness of a stock having a salt content of 0.3% and 5 ppm of an equimolar mixture of 1-(3-hydroxy-propyl)-3-((1S,2S,5R)-2-isopropyl-5-methyl-cyclohexyl)-urea (3) and 1-(3-hydroxy-propyl)-3-((1R,2R,5S)-2-isopropyl-5-methyl-cyclohexyl)-urea (4) added was tasted. The testers evaluated this stock against a reference series of this same stock with salt contents of 0.2%, 0.3%, 0.4% and 0.5%. The saltiness of the stock with a salt content of 0.3% and 5 ppm of an equimolar mixture of 1-(3-hydroxy-propyl)-3-((1S,2S,5R)-2-isopropyl-5-methyl-cyclohexyl)-urea (3) and 1-(3-hydroxy-propyl)-3-((1R,2R,5S)-2-isopropyl-5-methyl-cyclohexyl)-urea (4) added was evaluated with a saltiness of 0.36% on average.

In another test, the saltiness of a stock having a salt content of 0.3% and 3 ppm of an equimolar mixture of (3-methoxy-propyl)-carbamic acid (1S,2S,5R)-2-isopropyl-5-methyl-cyclohexyl ester (9) and (3-methoxy-propyl)-carbamic acid (1R,2R,5S)-2-isopropyl-5-methyl-cyclohexyl ester (10) was tasted. The testers evaluated this stock against a reference series of this same stock with salt contents of 0.2%, 0.3%, 0.4% and 0.5%. The saltiness of the stock with a salt content of 0.3% and 3 ppm of an equimolar mixture of (3-methoxy-propyl)-carbamic acid (1S,2S,5R)-2-isopropyl-5-methyl-cyclohexyl ester (9) and (3-methoxy-propyl)-carbamic acid (1R,2R,5S)-2-isopropyl-5-methyl-cyclohexyl ester (10) was evaluated with a saltiness of 0.35% on average.

Another aspect of the invention relates to the use of a mixture as a flavor material mixture, which consists of the following components or contains them:
(a) a compound selected from the group consisting of compounds of the formulae (I) and (ent-I) as defined above or a mixture consisting of two or more compounds or containing one or more compounds selected from the group consisting of compounds of the formulae (I) and (ent-I) as defined above (preferably according to one of the configurations referred to above as preferred)
and
(b) a compound selected from the group consisting of compounds of the formulae (II), (ent-II), (III), (ent-III), (IV), (ent-IV) or a mixture consisting of two or more compounds or containing one or more compounds selected from the group consisting of compounds of the formulae (II), (ent-II), (III), (ent-III), (IV), (ent-IV):

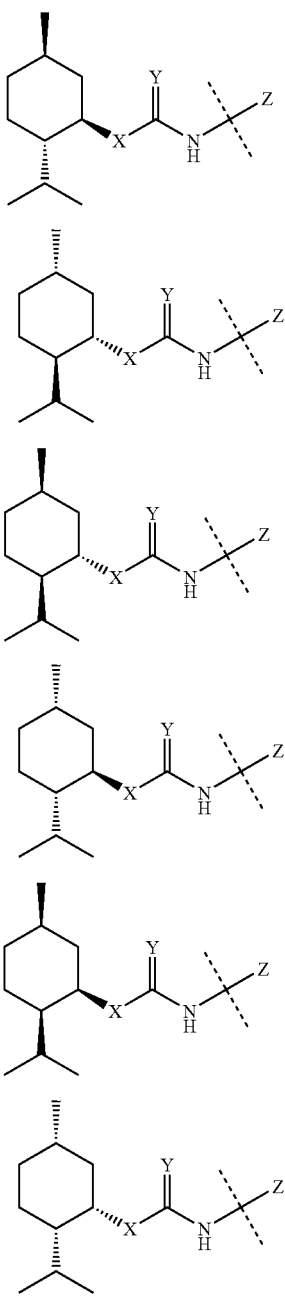

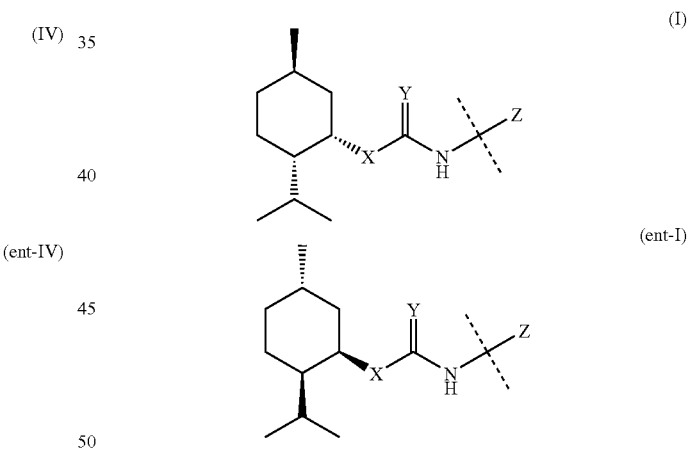

wherein X, Y and Z in the formulae (II), (ent-II), (III), (ent-III), (IV), (ent-IV) respectively have, independently of one another, one of the meanings specified above for the formulae (I) and (ent-I).

In the flavor material mixture defined above, the weight ratio of (a) the total amount of compounds of formulae (I) and (ent-I) to (b) the total amount of compounds of formulae (II), (ent-II), (III), (ent-III), (IV) and (ent-IV) in the flavor material mixture is preferentially (but not necessarily) at least 60:40, preferably at least 90:10, particularly preferably at least 95:5.

Correspondingly, the invention also relates to the particularly preferred to use of a compound of the formulae (I) and (ent-I) as defined above or a mixture consisting of two or more compounds or containing one or more compounds of the formulae (I) and (ent-I) or a mixture as defined above comprising (a) a compound of the formulae (I) and (ent-I) or a mixture containing or consisting of compounds of the formulae (I) and (ent-I) and (b) a compound of the formulae (II), (ent-II), (III), (ent-III), (IV), (ent-IV) as defined above or a mixture containing or consisting of compounds of the formulae (II), (ent-II), (III), (ent-III), (IV), (ent-IV) for producing, imparting, modifying and/or enhancing an umami flavor and/or saltiness. In respect of preferred compounds and mixtures, that stated above applies accordingly.

According to another aspect, the present invention relates to a method for producing, imparting, modifying and/or enhancing a flavor impression, in particular an umami flavor and/or saltiness. In the method according to the invention, a compound of the formulae (I) and (ent-I) as defined above or a mixture consisting of two or more compounds or containing one or more compounds of the formulae (I) and (ent-I) or a mixture as defined above comprising (a) a compound of the formulae (I) and (ent-I) or a mixture containing or consisting of compounds of the formulae (I) and (ent-I) and (b) a compound of the formulae (II), (ent-II), (III), (ent-III), (IV), (ent-IV) as defined above or a mixture containing or consisting of compounds of the formulae (II), (ent-II), (III), (ent-III), (IV), (ent-IV) is added to a substance or composition in an effective flavoring amount.

Another aspect of the invention relates to novel compounds of the formulae (I) and (ent-I), and to corresponding mixtures. Correspondingly, the invention relates to single compounds or mixtures consisting of two or more compounds or containing one or more compounds selected from the group consisting of compounds of the formulae (I) and (ent-I)

wherein the dashed line respectively marks the bond which links the organic residue Z to the neighboring nitrogen atom in formula (I) or (ent-I), and wherein the following apply independently of one another in the formulae (I) and (ent-I):

X=NH or O;

Y=O, S or NR1, where R1 denotes hydrogen, methyl, ethyl, propyl or isopropyl; and Z=organic residue consisting of carbon and hydrogen atoms and optionally oxygen atoms, wherein
  the sum of the number of carbon and oxygen atoms is at most 15 and the number of oxygen atoms is at most 4, and
  the atom by which the organic residue Z is bound to the neighboring nitrogen in formula (I) or (ent-I) is carbon, with the condition that the organic residue Z does not contain a C—C double or triple bond, contains at most one aromatic ring, and is not a group —C(=$Y^2$)—R2 in which $Y^2$ has any of the meanings specified above for Y and R2 is any organic residue, Z is not —C(R5)(R6)-C(=O)OR4, where R4 denotes H, methyl, ethyl, propyl, iso-propyl, butyl, iso-butyl or tert.-butyl and R5 and R6 independently of one another denote H or an organic residue, if X=NH and Y=O, then Z is not neomenthyl, 2-methyl-cyclohexyl or phenyl, and if X=NH and Y=S, then Z is not neomenthyl or phenyl, and if X=O and Y=O, then Z does not denote ethyl, hydroxy-ethyl, 1-phenylethyl, 2-phenylethyl, 2-hydroxy-1-methyl-2-phenylethyl, isopropyl, 2-hydroxy-1-methyl-ethyl, cyclohexyl, 4-hydroxyphenyl, 2-hydroxy-5-methylphenyl or 2,4,7-trioxa-3,3,8-trimethylbicyclo[3.3.0]octan-6-ylmethyl.

Compounds or mixtures as defined above are particularly preferred when the following apply (i) for the compound of formula (I) or (ent-I) or (ii) for one or more or all compounds of the formulae (I) and (ent-I) in the mixture:

X=NH or O;

Y=O;

Z=organic residue consisting of carbon and hydrogen atoms and optionally oxygen atoms, and the atom by which the organic residue Z is bound to the neighboring nitrogen in formula (I) or (ent-I) is carbon, with the condition that the organic residue Z does not contain a C—C double or triple bond, contains at most one aromatic ring, and is not a group —C(=$Y^2$)—R2 in which $Y^2$ has any of the meanings specified above for Y and R2 is any organic residue.

Single compounds or mixtures as defined above are also particularly preferred when the following apply (i) for the compound of formula (I) or (ent-I) or (ii) for one or more or all compounds of the formulae (I) and (ent-I) in the mixture:

Y=O; and

Z=organic residue in which the sum of the number of carbon and oxygen atoms is at most 11 and the number of oxygen atoms is at most 2, where Z is a residue selected from the group consisting of optionally singly or multiply substituted alkyl, $C_3$-$C_7$ cycloalkyl, phenyl and phenylalkyl, one or more substituents optionally present in the residue Z being selected from the group consisting of OH, $C_1$-$C_4$ alkoxy, $C_1$-$C_4$ alkoxycarbonyl and cyclic ether, in which case cyclic groups in the organic residue are optionally substituted by $C_1$-$C_4$ alkyl groups.

Single compounds or mixtures as defined above are particularly preferred when the organic residue Z (i) for the compound of formulae (I) or (ent-I) or (i) for one or more or all compounds of the formulae (I) and (ent-I) in the mixture is selected from the group consisting of:

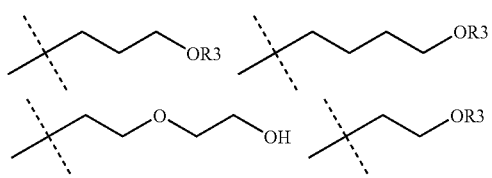

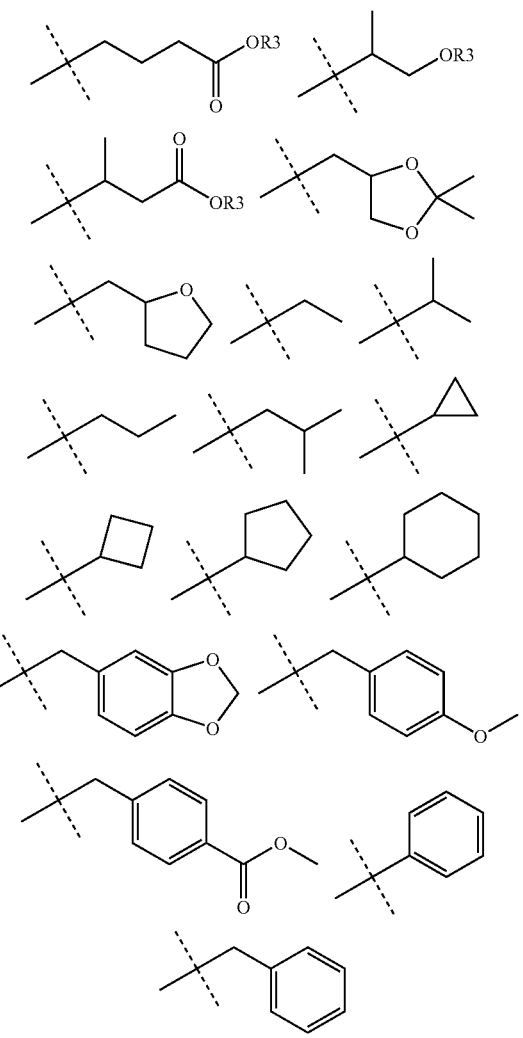

wherein optionally present residues R3 independently of one another denote hydrogen, methyl, ethyl, n-propyl, iso-propyl, n-butyl, iso-butyl and the dashed line respectively marks the bond which links the organic residue Z to the neighboring nitrogen atom in formula (I) or (ent-I).

Single compounds or mixtures as defined above are also particularly preferred when the following apply (i) for the compound of formula (I) or (ent-I) or (ii) for one or more or all compounds of the formulae (I) and (ent-I) in the mixture:

Y=O; and

Z=organic residue in which the sum of the number of carbon and oxygen atoms is at most 11 and the number of oxygen atoms is at most 2, where Z is an optionally singly or multiply substituted straight-chained or branched $C_1$-$C_6$ alkyl residue, one or more optionally present substituents preferably being selected from the group consisting of OH, $C_1$-$C_4$ alkoxy and $C_1$-$C_4$ alkoxycarbonyl.

Single compounds or mixtures as defined above are also particularly preferred when (i) the compound of formula (I) and (ent-I) or (ii) one, two, more than two or all compounds of the formulae (I) and (ent-I) in the mixture are selected from the group consisting of:

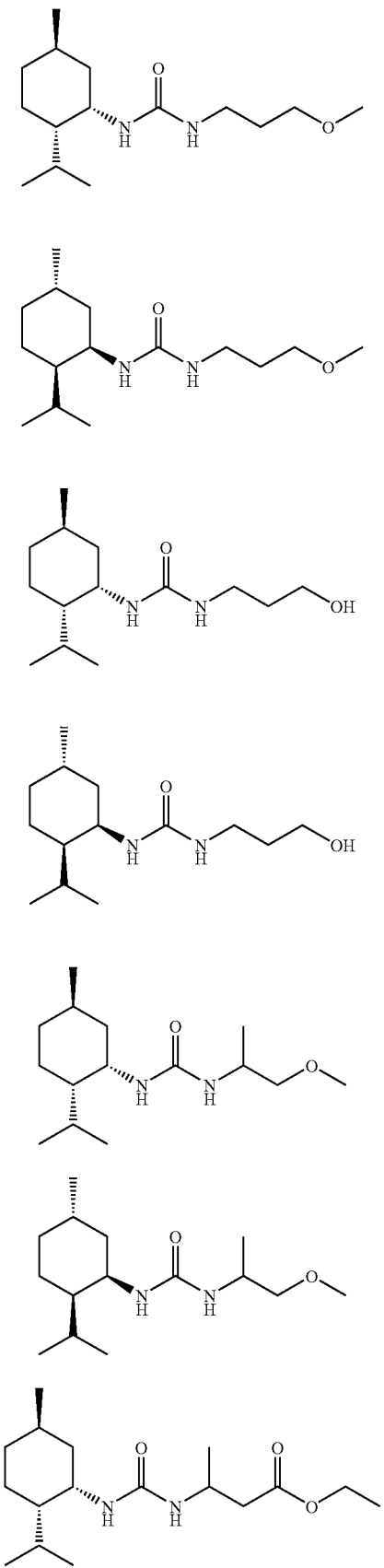
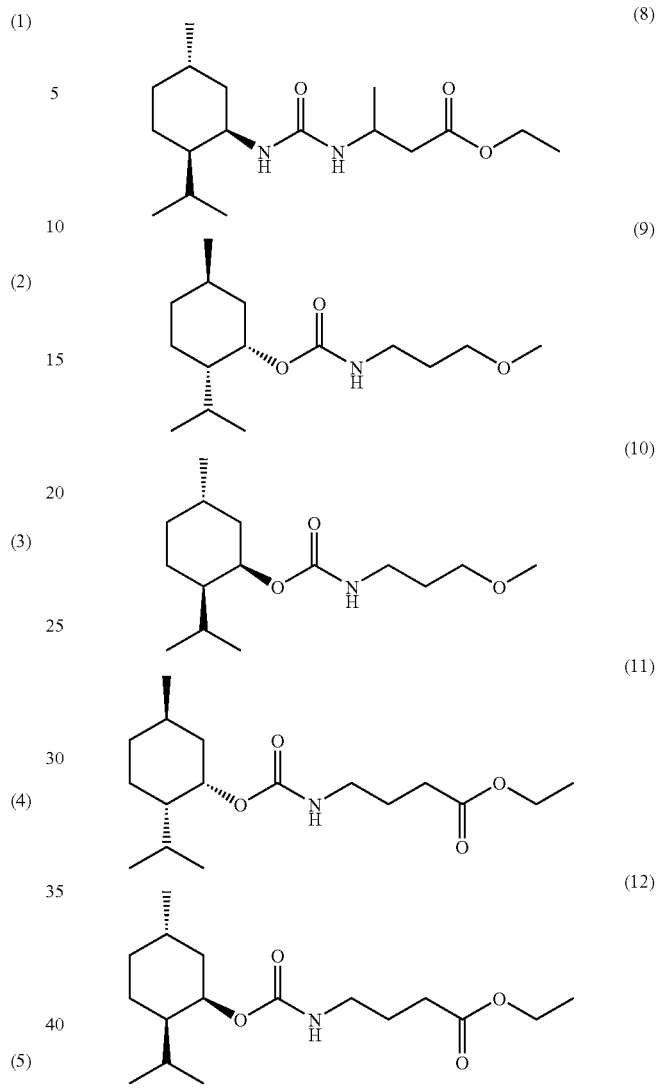

(1) 1-((1S,2S,5R)-2-isopropyl-5-methyl-cyclohexyl)-3-(3-methoxy-propyl)-urea,
(2) 1-((1R,2R,5S)-2-isopropyl-5-methyl-cyclohexyl)-3-(3-methoxy-propyl)-urea,
(3) 1-(3-hydroxy-propyl)-3-((1S,2S,5R)-2-isopropyl-5-methyl-cyclohexyl)-urea,
(4) 1-(3-hydroxy-propyl)-3-((1R,2R,5S)-2-isopropyl-5-methyl-cyclohexyl)-urea,
(5) 1-((1S,2S,5R)-2-isopropyl-5-methyl-cyclohexyl)-3-(2-methoxy-1-methyl-ethyl)-urea,
(6) 1-((1R,2R,5S)-2-isopropyl-5-methyl-cyclohexyl)-3-(2-methoxy-1-methyl-ethyl)-urea,
(7) 3-[3-((1S,2S,5R)-2-isopropyl-5-methyl-cyclohexyl)-ureido]-butyric acid ethyl ester,
(8) 3-[3-((1R,2R,5S)-2-isopropyl-5-methyl-cyclohexyl)-ureido]-butyric acid ethyl ester,
(9) (3-methoxy-propyl)-carbamic acid (1S,2S,5R)-2-isopropyl-5-methyl-cyclohexyl ester,
(10) (3-methoxy-propyl)-carbamic acid (1R,2R,5S)-2-isopropyl-5-methyl-cyclohexyl ester,
(11) 4-((1S,2S,5R)-2-isopropyl-5-methyl-cyclohexyloxycarbonylamino)-butyric acid ethyl ester
(12) 4-((1R,2R,5S)-2-isopropyl-5-methyl-cyclohexyloxycarbonylamino)-butyric acid ethyl ester.

Mixtures as defined above are likewise preferred when the mixtures contain one or more pairs of compounds of formulae (I) and (ent-I) or consist of one or more such pairs, each pair consisting of a compound of the formula (I) and a compound of the formula (ent-I) as defined above, wherein the meanings of X and Y in the compound of formula (I) are respectively identical to the meanings of X and Y in the compound of formula (ent-I) and wherein (a) the meaning of Z in the compound of formula (I) is identical to the meaning of Z in the compound of formula (ent-I) or (b) Z in the compound of formula (I) and Z in the compound of formula (ent-I) contain or one or more chiral centers and differ only by the absolute configuration at one, several or all of these chiral centers, wherein each pair is preferably an enantiomer or epimer pair.

Mixtures which consist of the following components or contain them are likewise preferred:

(a) a compound selected from the group consisting of compounds of the formulae (I) and (ent-I) as defined above or a mixture consisting of two or more compounds or containing one or more compounds selected from the group consisting of compounds of the formulae (I) and (ent-I) as defined above or a mixture consisting of or containing a mixture as defined above; and (b) a compound selected from the group consisting of compounds of the formulae (II), (ent-II), (III), (ent-II), (IV), (ent-IV) or a mixture consisting of two or more compounds or containing one or more compounds selected from the group consisting of compounds of the formulae (II), (ent-II), (III), (ent-III), (IV), (ent-IV):

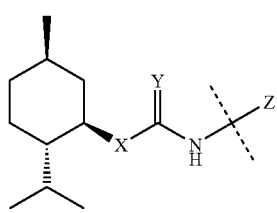
(II)

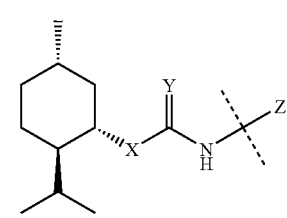
(ent-II)

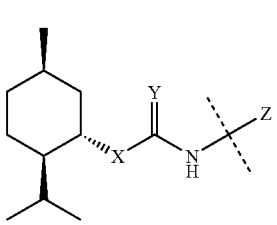
(III)

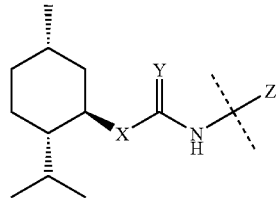
(ent-III)

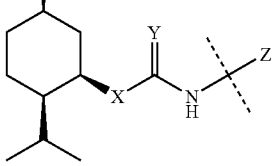
(IV)

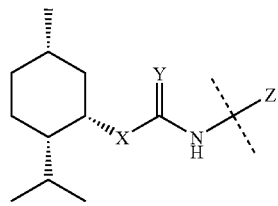
(ent-IV)

wherein X, Y and Z in the formulae (II), (ent-II), (III), (ent-III), (IV), (ent-IV) respectively have, independently of one another, one of the meanings specified above for the formulae (I) and (ent-I)

and wherein in the material mixture defined above, the weight ratio of (a) the total amount of compounds of formulae (I) and (ent-I) to (b) the total amount of compounds of formulae (II), (ent-II), (III), (ent-III), (IV) and (ent-IV) in the flavor material mixture is preferentially (but not necessarily) at least 60:40, preferably at least 90:10, particularly preferably at least 95:5.

The following compounds already known in the literature are not the preferred subject-matter of the present invention: the dineomenthylurea derivative—which has also been described without defined stereochemistry (*Mikrochimica Acta* 1989, 3 (1-2), 117-24)- and the dineomenthylthiourea derivative (ARKIVOK, 2007, 7, 157-166) as well as the dineomenthylguanidine derivative (*Chin. J. Chem.* 2000, 18 (3) 411-413; *Tetrahedron:Asymmetry* 1999, 10 (4), 713-719)) are already known in the literature, although no information is given about the flavor of these compounds:

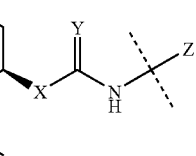

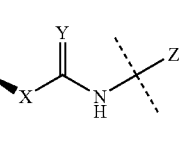

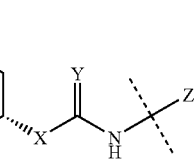

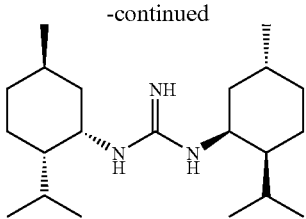

Likewise known in the literature are both enantiomeric isopropylcarbamate derivatives (*Angew. Chem.* 1982, 94 (9), 709-10) and a variant not further described stereochemically (20th *Pept., Proc. Eur. Pept. Symp.* 1989, 16-18). Here again, the flavor properties have not been described:

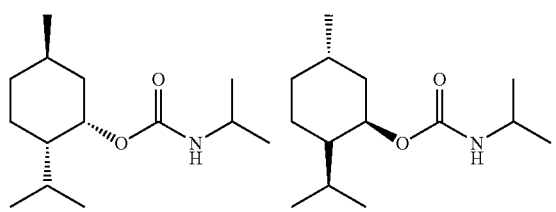

The phenyl-substituted urea derivative has already been known for a long time. Some physical properties have been characterized, but no information is given about the flavor (*J. Chem. Soc.* 1951, 2968-2972):

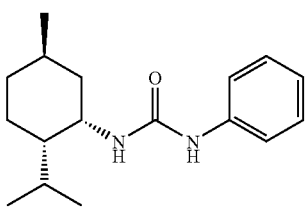 [SMILES: CC(C)[C@@H]1CC[C@@H](C)C[C@@H]1NC(=O)Nc1ccccc1]

This structure—and its thio analog—is likewise repeatedly described but not in a stereochemically unique way (inter alia *J. Chem. Soc.* 1926, 2209-2223; *J. Chem. Soc.* 1926, 2223-2234, *Chem. Ber.* 1958, 91, 311-319). Information is likewise not given about the flavor:

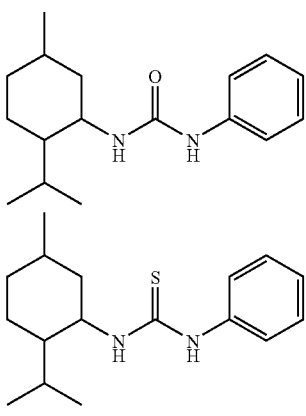

Lastly, the carbamate known by the CAS number [585829-94-5] is commercially available, and is also already known in the literature without accurate information of the stereochemistry (*J. Chem. Soc., Trans* 1911, 1337-1340). Here again, however, no flavor properties are known:

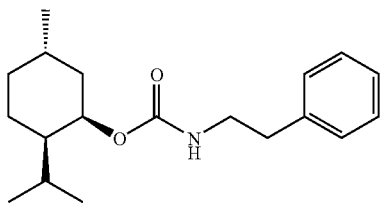 [SMILES: CC(C)[C@H]1CC[C@H](C)C[C@H]1OC(=O)NCCc1ccccc1]

Furthermore, the following compounds are not preferred for the purposes of the invention or are preferred only in exceptional cases:

Compounds of the formulae (I) or (ent-I), where Z represents an α-carbonyl group.

In particular corresponding derivatives with an α-carboxyl group, as are widely described in the literature, are not preferred.

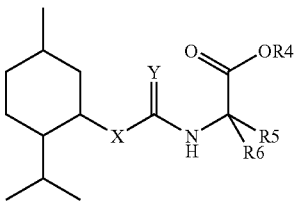

In this case, R4 denotes H, methyl, ethyl, propyl, iso-propyl, butyl, iso-butyl or tert.-butyl, R5 and R6 independently of one another denote H or an organic residue, and that stated for the formulae (I) and (ent-I) applies for X and Y. However, nothing is known about the flavor of such derivatives. In particular, the known diastereomeric thiourea derivatives (*Anal. Chim. Acta* 1978, 101 (1), 111-116) with a (+)-neo-menthyl basic structure are excluded, which have been obtained by reacting neo-menthyl isothiocyanate with the free amino function of various amino acids of the D- and L-series (AS=alanine, valine, norvaline, leucine, norleucine, isoleucine, proline, phenylglycine, phenylalanine, serine, threonine, asparagic acid and glutamic acid):

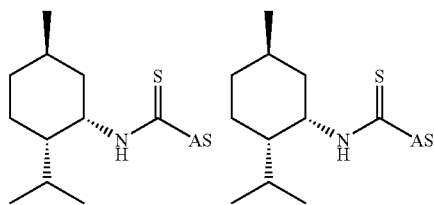

The ethyl-substituted carbamate has already been described (*Ann. Chim.* 1954, 257-309) and is employed as (−)-menthol derivative by Givaudan in WO 2004/000023 as an insect repellent. No information is given about the flavor properties:

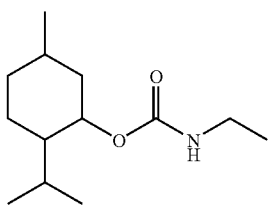 [SMILES: CCNC(=O)OC1CC(C)CCC1C(C)C]

A methylcyclohexyl-substituted urea derivative has likewise been described without studies of the flavor (*Sitzb. Ges. Beforderung gesamten Naturwissenschaften Marburg* 62 (4), 113-35):

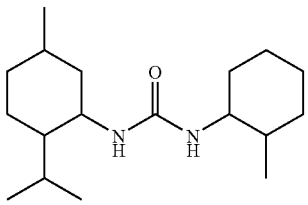 [SMILES: CC1CCC(C(C)C)C(NC(=O)NC2CCCCC2C)C1]

A Cyclohexyl-substituted carbamate derivative is disclosed in U.S. Pat. No. 6,531,506 and U.S. Pat. No. 5,955,496 as an epoxide hydrolase inhibitor, and has also already been described earlier in studies into the reaction of cyclohexyl-isothiocyanates with food ingredients (*Deutsche Lebensmittel-Rundschau* 1984, 80 (6), 170-174). However, information about the flavor is not given.

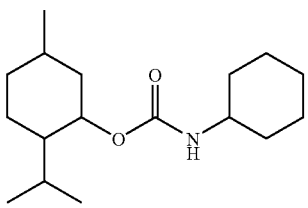 [SMILES: CC1CCC(C(C)C)C(OC(=O)NC2CCCCC2)C1]

Another aryl-substituted carbamate derivative has likewise been described without further studies into the flavor of this compound (*Organic Mass Spectrometry* 1971, 5 (2), 157-169):

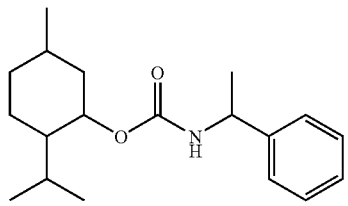 [SMILES: CC1CCC(C(C)C)C(OC(=O)NC(C)c2ccccc2)C1]

The following hydroxyaryl-substituted carbamate has likewise been described (*Annales Pharmaceutiques Francaises* 1958, 16, 408-413), although nothing has been reported about the flavor of this compound:

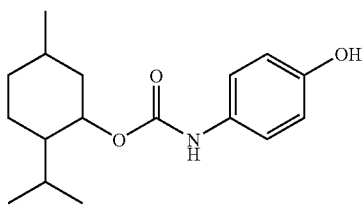 [SMILES: CC1CCC(C(C)C)C(OC(=O)Nc2ccc(O)cc2)C1]

The use of the following carbamate in cosmetic applications is described in WO 2002/002071:

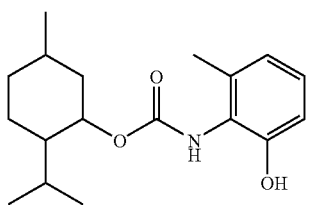 [SMILES: Cc1cccc(O)c1NC(=O)OC1CC(C)CCC1C(C)C]

DE4226043 is likewise discloses to carbamates with non-specific stereochemistry as cooling agents without a problematic intrinsic smell or intrinsic flavor, the flavorless and the measured rotation value suggesting the use of (−)-menthol as the starting material:

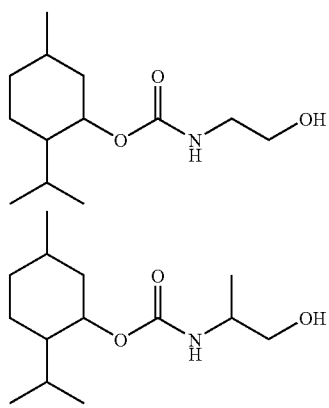

The following derivative is also based on a carbamate structure (*J. Chem. Soc., Chem. Commun.* 1992, 18, 1308-1310; *Tetrahedron Lett.* 1991, 32 (34), 4251-4254). Here again, no studies have been undertaken regarding the flavor.

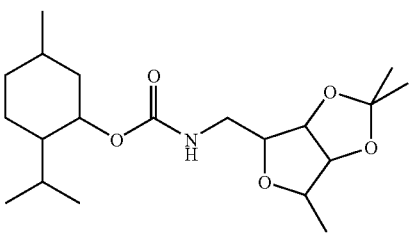 [SMILES: CC1CCC(C(C)C)C(OC(=O)NCC2OC(C)C3OC(C)(C)OC23)C1]

Lastly, the following carbamate derivative is registered under the CAS number [200123-67-7] without mentioning data and properties:

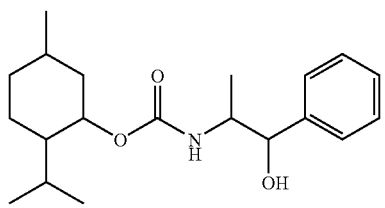 [SMILES: CC1CCC(C(C)C)C(OC(=O)NC(C)C(O)c2ccccc2)C1]

All the aforementioned compounds known in the literature are not preferred for the purposes according to the invention. Furthermore, there are also a multiplicity of derivatives which are based on a diastereomeric methyl basic structure but are not discussed in the present text owing to their unsuitable stereochemistry.

According to another aspect, the present invention also relates to compositions and preparations, in particular compositions and preparations suitable for consumption, comprising or consisting of an effective flavoring amount of a compound of the formulae (I) and (ent-I) as defined above or any mixture as defined above or a mixture as defined above comprising (a) one or more compounds of the formulae (I) and (ent-I) and (b) one or more compounds of the formulae (II), (ent-II), (III), (ent-III), (IV), (ent-IV) and one or more further ingredients suitable for consumption. In respect of preferred compounds and mixtures, that stated above applies accordingly.

The preparations or compositions suitable for consumption according to the invention, used for staple foods, oral care or luxury foods, are regularly products which are intended to be introduced into the human oral cavity, remain there for a particular time and subsequently either be consumed (for example food ready for consumption, see also below) or removed from the oral cavity (for example chewing gums or toothpastes). These products include all materials or goods which are intended to be taken by humans in a process, partially processed or unprocessed state. These also include materials which are added to foods during their production, processing or treatment and are intended to be introduced into the human oral cavity.

In the scope of the present text, a "food" is to mean in particular materials which are intended to be swallowed in the unmodified, prepared or processed state by humans and then digested; food is to this extent also to mean encapsulations, coatings or other coverings which intended to be swallowed as well, or for which swallowing is foreseeable. Certain products which are conventionally removed again from the oral cavity (for example chewing gums) are also to be understood as food in the scope of the present text, since in their case the possibility that they may be at least partially swallowed cannot be ruled out.

A food ready for consumption is in this case to mean a food which is already fully constituted in respect of the substances crucial for the flavor. The term "food ready for consumption" also includes drinks as well as solid or semisolid food ready for consumption. Examples which may be mentioned are deep-frozen products which need to be thawed and heated to eating temperature before consumption. Products such as yogurt or ice cream, but also chewing gums or hard caramels, are included as food ready for consumption.

A semifinished product in the context of the present text is to mean a product which is unsuitable for use as a food ready for consumption owing to a very high content of aromatizing and flavoring substances. The semifinished product is not converted into a food ready for consumption until it has been mixed with at least one further constituent (i.e. reducing the concentration of the relevant aromatizing and flavoring substances) and optionally further process steps (for example heating, freezing). Examples of semifinished products which may be mentioned here are packet soups, baking aromas and pudding powders.

An oral care product (also referred to as an oral hygiene product or oral hygiene preparation) in the sense of the invention is to mean one of the formulations familiar to the person skilled in the art for cleaning and care of the oral cavity and the nasal cavity and for freshening the breath. Here, care of the teeth and gums is expressly included. Administration forms of conventional oral hygiene formulations are in particular creams, gels, pastes, foams, emulsions, suspensions, aerosols, sprays, as well as capsules, granules, pastilles, tablets, sweets or chewing gums, this list not being meant to imply limitation for the purposes of this invention.

Preferred oral care products (oral hygiene products) in particular those in the form of toothpaste, tooth cream, tooth gel, tooth powder, tooth cleaning liquid, tooth cleaning foam, mouthwash, tooth cream and mouthwash as a 2-in-1 product, sucking sweets, a mouth spray, dental floss or tooth cleaning chewing gum.

Chewing gums generally comprise a chewing gum base, a chewing gum base, i.e. a chewing compound which becomes plastic when chewed, various types of sugar, sugar substitutes, other sweet-tasting substances, sugar alcohols, sorbitol, xylitol, mannitol), agents with a cooling effect, flavor correctors for unpleasant flavor impressions, other flavor-modulating substances (for example inositol phosphate, nucleotides such as guanosine monophosphate, adenosine monophosphate or other substances such as sodium glutamate or 2-phenoxypropionic acid), humectants, thickeners, emulsifiers, stabilizers, odor correctors and aromas (for example: eucalyptus-menthol, cherry, strawberry, grapefruit, vanilla, banana, citrus, peach, blackcurrant, tropical fruits, ginger, coffee, cinnamon, combinations (of the said aromas) with mint aromas, as well as spearmint and peppermint on their own). It is also particularly beneficial to combine the aromas with other substances which have cooling, warming and/or mouth water in properties. Many different chewing gum bases are known in the prior art, and distinction is to be made between so-called "chewing gum" or "bubble gum" base, the latter being softer so that chewing gum bubbles can also be formed. Besides traditionally used natural resins or the natural latex chicle, customary chewing gum bases nowadays usually comprise elastomers such as polyvinyl acetates (PVA), polyethylenes, (low or medium molecular weight) polyisobutenes (PIB), polybutadienes, isobutene-isoprene copolymers (butyl rubber), polyvinyl ethyl ether (PVE), polyvinyl butyl ether, copolymers of vinyl esters and vinyl ethers, styrene-butadiene copolymers (styrene-butadiene rubber, SBR) or vinyl elastomers, for example based on vinyl acetate/vinyl laurate, vinyl acetate/vinyl stearate or ethylene/vinyl acetate, as well as mixtures of the said elastomers, as described for example in EP 0 242 325, U.S. Pat. No. 4,518, 615, U.S. Pat. No. 5,093,136, U.S. Pat. No. 5,266,336 U.S. Pat. No. 5,601,858 or U.S. Pat. No. 6,986,709. Chewing gum bases furthermore comprise other constituents, for example (inorganic) fillers, softeners, emulsifiers, antioxidants, waxes, fats or fatty oils, for example hardened (hydrogenated) plant or animal fats, mono-, di- or triglycerides. Suitable (inorganic fillers) are for example calcium carbonate, titanium dioxide, silicon dioxide, talc, aluminum oxide, dicalcium phosphate, tricalcium phosphate, magnesium hydroxide and mixtures thereof. Suitable softeners or detackifiers are for example lanolin, stearic acid, sodium stearate, ethyl acetate, diacetine (glycerine diacetate), triacetine (glycerine triacetate), triethyl citrate. Suitable waxes for example paraffin waxes, candelilla wax, carnauba wax, microcrystalline waxes and polyethylene waxes. Suitable emulsifiers are for example phosphatides such as lecithin, mono- and diglycerides of fatty acids, for example glycerine monostearate.

A range of compositions according to the invention are preferred. These include compositions, in particular a composition suitable for consumption, comprising or consisting of an effective flavoring amount of a compound or a mixture as defined above and one or more further constituents suitable for consumption. Such preferably spray-dried compositions, which comprise solid excipients and optionally aromatizing compositions as constituents suitable for consumption, are particularly preferred. Compositions as described above are likewise preferred when the compositions are spray-dried.

A (preferably spray-dried) composition which, besides an effective flavoring amount of one or more compounds of the formulae (I) and (ent-I) or a mixture as defined above comprising (a) one or more compounds of the formulae (I) and (ent-I) and (b) one or more compounds of the formulae (II), (ent-II), (III), (ent-III), (IV), (ent-IV), comprises one or more solid excipients suitable for consumption, is particularly preferred. In respect of preferred compounds and mixtures, that stated above applies accordingly.

Advantageous excipients to be mentioned in these preferred (preferably spray-dried) compositions according to the invention are silicon dioxide (silica, silica gel), carbohydrates and/or carbohydrate polymers (polysaccharides), cyclodextrins, starches, disaggregated starches (starch hydrolysates), chemically or physically modified starches, modified celluloses, gum arabic, ghatti gum, traganth, karaya, carrageenan, guar seed flour, carob bean powder, alginates, pectin, inulin or xanthan gum. Preferred starch hydrolysates are maltodextrins and dextrins.

Preferred excipients are silicon dioxide, gum arabic and maltodextrins, in which case maltodextrins with DE values in the range of from 5 to 20 are in turn preferred. The plants which originally provided the starches for producing the starch hydrolysates are not important. Corn-based starches and starches from tapioca, rice, wheat or potato are suitable and readily available. The excipients may also function as anticaking agents, for example like silicon dioxide.

The compositions according to the invention which also comprise one or more solid excipients, besides the compound or compounds of the formulae (I) and (ent-I) or mixture or mixtures as defined above to be used according to the invention, may for example be produced by mechanical mixing processes, in which case comminution of the particles may also take place simultaneously, or by means of spray drying. Compositions according to the invention which comprise solid excipients and are produced by means of spray drying are preferred; in respect of spray drying, reference is made to U.S. Pat. No. 3,159,585, U.S. Pat. No. 3,971,852, U.S. Pat. No. 4,532,145 or U.S. Pat. No. 5,124,162.

Preferred compositions according to the invention comprising excipients, which have been produced by means of spray drying, have an average particle size in the range of from 30 to 300 μm and a residual moisture content of less than or equal to 5 wt. %.

The weight ratio of the total mass of the compounds of formulae (I) and (ent-I), or—when using the mixtures defined above—the weight ratio of the total mass of the compounds of formulae (I) and (ent-I), (II), (ent-II), (III), (ent-III), (IV), (ent-IV), to the solid excipient or excipients suitable for consumption preferentially lies in the range of from 1:10 to 1:100000, preferably in the range of from 1:50 (preferentially 1:100) to 1:20000, particularly preferably in the range of from 1:100 (preferentially 1:1000) to 1:5000, expressed in terms of the dry mass of the composition.

In the composition according to the invention, the sum of the constituents comprising (i) compounds of the formulae (I) and (ent-I) or mixtures as defined above comprising (a) one or more compounds of the formulae (I) and (ent-I) and (b) one or more compounds of the formulae (II), (ent-II), (III), (ent-III), (IV), (ent-IV) and (ii) excipients, preferentially lies in the range of from 70 to 100 wt. %, preferably in the range of from 85 to 100 wt. %.

The invention also relates to a (preferably spray-dried) composition which, besides (i) an effective flavoring amount of one or more compounds of the formulae (I) and (ent-I) or a mixture as defined above comprising (a) one or more compounds of the formulae (I) and (ent-I) and (b) one or more compounds of the formulae (II), (ent-II), (III), (ent-III), (IV), (ent-IV) and (ii) solid excipients, also comprises (iii) one or more aromatizing compositions, or consists of the said components. In respect of preferred compounds and mixtures, that stated above applies accordingly.

Such an aromatizing composition in the sense of the present invention comprises at least one volatile aromatizing substance (here, however, this is not intended to mean compounds of the formulae (I) and (ent-I) or mixtures to be used according to the invention as defined above). The volatile aromatizing substance is preferably a sensorially acting component with a vapor pressure of greater than or equal to 0.01 Pa at 25° C., preferably a vapor pressure of greater than or equal to 0.025 Pa at 25° C. A large number of volatile aromatizing substances have a vapor pressure of greater than or equal to 1 Pa at 25° C., and these aromatizing substances are regarded as preferred for use in compositions according to the invention.

Examples of aromatizing substances which may be a constituent of the aromatic composition may be found for example in K. Bauer, D. Garbe and H. Surburg, Common Fragrance and Flavor Materials, 4$^{th}$. Ed., Wiley-VCH, Weinheim 2001. The following may for example be mentioned: organic acids (saturated and unsaturated) such as for example butyric acid, acetic acid, methylbutyric acid, hexanoic acid; alcohols (saturated and unsaturated) such as for example ethanol, propylene glycol, octenol, cis-3-hexenol, benzyl alcohol; sulfides and disulfides such as for example dimethyl sulfide, difurfuryl disulfide, methyl thiopropanal; thiols such as for example methyl furanthiol; pyrazines and pyrrolines such as for example methylpyrazine, acetyl pyrazine, 2-propionyl pyrroline, 2-acetyl-pyrroline.

The aromatizing compositions may also be used in the form of reaction aromas (Maillard products) and/or extracts or enteric oils of planets or plant components or fractions thereof.

Another preferred composition according to the invention is suitable for consumption, which comprises (a) one or more single compounds of the formulae (I) and (ent-I) to be used according to the invention or (b) a mixture as defined above, is a water-in-oil (W/O) emulsion. Besides the compound or compounds of the formulae (I) and (ent-I) to be used according to the invention, or the mixtures as described above, such an emulsion comprises water, an oil phase, one or more W/O emulsifiers, optionally one or more antioxidants and optionally one or more substances to enhance an antioxidant effect. In respect of preferred compounds and mixtures, that stated above applies accordingly.

Compositions suitable for consumption as defined above are particularly preferred when the composition is a water-in-oil emulsion comprising water, an oil phase, one or more water-in-oil emulsifiers and optionally one or more antioxidants and optionally one or more substances to enhance an antioxidant effect.

Such a compound according to the invention (W/O emulsion) preferably comprises
- in total 0.01 to 0.1 wt. % compounds of the formulae (I) and (ent-I) or—when using one of the mixtures defined above—compounds of the formulae (I), (ent-I), (II), (ent-II), (III), (ent-III), (IV), (ent-IV)
- 5 to 30 wt. %, preferably 8 to 25 wt. % water,
- 50 to 90 wt. %, preferably 60 to 80 wt. % of an oil phase,
- 0.1 to 5 wt. % of an edible W/O emulsifier
- expressed in terms of the total mass of the composition
- and optionally one or more antioxidants and optionally one or more substances to enhance an antioxidant effect.

Such a W/O emulsion according to the invention particularly preferably consists of the said constituents in the said amounts.

The oil phase of such a W/O emulsion according to the invention comprises (or consists of) preferably a fatty oil and/or an aromatizing composition. Oil phases comprising or consisting of a fatty oil and an aromatizing composition are preferred.

For example edible oils, in particular plant oils, are suitable as fatty oils. Suitable fatty oils are for example borage oil, thistle oil, groundnut oil, hazelnut oil, cocoa oil, pumpkin seed oil, linseed oil, corn seed oil, macadamia nut oil, almond oil, olive oil, palm seed oil, pecan nut oil, pistachio seed oil, rape oil, rice germ oil, sesame oil, soya oil, sunflower oil, walnut oil or wheatgerm oil, or fractions obtainable therefrom. It is also possible to use liquid neutral esters based on medium-chained fatty acids and glycerine, for example Miglyols (for example Miglyol 810, Miglyol 812). Sunflower oil, palm seed oil and rape oil are preferred. Fractionated cocoa oils, which primarily have fatty acid residues with 6 to 8 C atoms, are furthermore preferably used. These are distinguished by their flavor neutrality and by their good oxidation stability.

The edible W/O emulsifiers is preferably selected from the group consisting of lecithin (E 322), mono- and diglycerides of edible fatty acids (E 471), acetic acid monoglycerides (E 472a), lactic acid monoglycerides (E 472b), citric acid monoglycerides (E 472c), tartaric acid monoglycerides (E 472d), diacetyl tartaric acid monoglycerides (E 472e), sorbitan monostearate (E 491).

Suitable antioxidants, and substances which can enhance the antioxidant effect, are the naturally occurring tocopherols and their derivatives, tocotrienols, flavonoids, ascorbic acid and its salts, alpha-hydroxy acids (for example citric acid, lactic acid, malic acid, tartaric acid) and their Na, K and Ca salts, ingredients isolated from plants, extracts or fractions thereof, for example from tea, green tea, algae, rapeseed, wheatgerm, rosemary, oregano, flavonoids, quercetin, phenolic benzyl amines. Propyl gallate, octyl gallate, dodecyl gallate, butylhydroxyanisol (BHA), butylhydroxytoluene (BHT), lecithins, mono- and diglycerides of edible fatty acids esterified with citric acid, orthophosphates and Na, K and Ca salts of monophosphoric acid and ascorbyl palmitate are furthermore suitable as antioxidants.

The W/O emulsions according to the invention are suitable in particular for application to food surfaces, the foods preferably having a water content of at most 10 wt. %, preferably at most 5 wt. %. In a preferred embodiment, the W/O emulsion has a sufficiently low viscosity at the application temperature so that it is possible to apply the W/O emulsion by means of spraying. Preferred foods, onto the surfaces of which a W/O emulsion according to the invention can be applied, are for example crackers, chips (for example based on potatoes, corn, cereals or bread), extruded snack articles (nibbles, flips) or baked snacks (for example salt sticks). W/O emulsions according to the invention are regularly applied in an amount of from 0.5 to 6 wt. % onto the food surfaces, expressed in terms of the total weight of the food.

As already mentioned, one aspect of the present invention relates to the use of a compound of the formulae (I) and (ent-I) defined above, in particular the compounds (1) to (6) indicated above as preferred, or the mixtures defined above comprising (a) one or more compounds of the formulae (I) and (ent-I) and (b) one or more compounds of the formulae (II), (ent-II), (III), (ent-III), (IV), (ent-IV) for producing, imparting, modifying and/or enhancing an umami flavor.

The compounds of the formulae (I) and (ent-I) (in an effective flavoring amount), the mixtures defined above comprising (a) one or more compounds of the formulae (I) and (ent-I) and (b) one or more compounds of the formulae (II), (ent-II), (III), (ent-III), (IV), (ent-IV) or the compositions according to the invention as defined above are preferably used in (i) preparations ready for use or consumption or (ii) semifinished products, used for staple or luxury foods, in particular sodium glutamate-reduced or -free preparations used in staple or luxury foods. In respect of preferred compounds and mixtures, that stated above applies accordingly.

It is likewise particularly preferable to use compounds or mixtures consisting of two or more compounds or containing one or more compounds selected from the group consisting of compounds of the formulae (I) and (ent-I) as defined above, or compositions as defined above, in
(i) preparations ready for use or consumption or
(ii) semifinished products,
used for staple or luxury foods, in particular sodium glutamate-reduced or -free preparations used in staple or luxury foods.

The term "sodium glutamate-reduced" in this case means that the preparation or semifinished product according to the invention contains significantly less sodium glutamate than is contained in the conventional preparation or semifinished product; the sodium glutamate content is then 5 to <100 wt. %, preferably 10 to 50 wt. %, particularly preferably 10 to 50 wt. % less than the sodium glutamate content of the conventional preparation. If there is also sodium glutamate in a preparation or semifinished product according to the invention in addition to the one or more compounds of the formulae (I) and (ent-I) or a mixture as defined above comprising (a) one or more compounds of the formulae (I) and (ent-I) and (b) one or more compounds of the formulae (II), (ent-II), (III), (ent-III), (IV), (ent-IV), then the weight ratio of the total amount of compounds of the formulae (I) and (ent-I) or mixtures as defined above to sodium glutamate preferably lies in the range of from 1:1 to 1:200.

The invention also relates to preparations comprising compounds or mixtures consisting of two or more compounds of the formulae (I) and (ent-I) or containing one or more compounds selected from the group consisting of as defined above or compositions as defined above.

Preparations according to the invention ready for use or consumption used for staple or luxury foods are preferred when they contain one or more compounds of the formulae (I) and (ent-I) to be used according to the invention or—when using the mixtures defined above—compounds of the formulae (I), (ent-I), (II), (ent-II), (III), (ent-III), (IV), (ent-IV), preferably in an amount in the range of from 0.01 ppm to 100 ppm, preferably in the range of from 0.1 ppm to 50 ppm, particularly preferably in the range of from 0.5 ppm (preferentially 1 ppm) to 30 ppm expressed in terms of the total weight of the preparation ready for use or consumption.

The invention also relates to a semifinished products comprising compounds or mixtures consisting of two or more compounds or containing one or more compounds selected from the group consisting of compounds of the formulae (I) and (ent-I) as described above or compositions as defined above.

Semifinished products according to the invention for the production of preparations ready for use or consumption used for staple or luxury foods are preferred when they contain one or more compounds of the formulae (I) and (ent-I) to be used according to the invention or—when using the mixtures defined above—compounds of the formulae (I), (ent-I), (II), (ent-II), (III), (ent-III), (IV), (ent-IV), preferably in an amount in the range of from 10 ppm to 100000 ppm (preferentially up to 800 ppm), preferably in the range of from 25 ppm to 5000 ppm (preferentially up to 750 ppm), particularly preferably in the range of from 50 ppm to 1200 ppm (preferentially up to 700 ppm) expressed in terms of the total weight of the semifinished product.

Sodium glutamate-reduced preparations according to the invention are particularly relevant when they contain sodium glutamate, of the amount of sodium glutamate not being sufficient to be perceived as a satisfactory umami flavor in a comparative preparation which does not contain a mixture according to the invention but is otherwise composed identically (normal sodium glutamate-reduced preparation), and the amount of the mixture according to the invention is sufficient to achieve a satisfactory umami flavor impression.

The preparations used for staple or luxury food in the sense of the invention are in particular bakery items (for example bread, biscuits, cakes, other pastries), beverages (for example vegetable juices, vegetable juice preparations), instant beverages (for example instant vegetable beverages), meat products (for example ham, fresh sausage of raw sausage preparations, spiced or marinated fresh or salt meat products), spiced or marinated fish products (for example surimi), eggs or egg products (dried egg, egg white, egg yolk), cereal products (for example precooked ready rice products, rice flour products, millet and sorghum products, raw or precooked noodles and pasta products), milk products (for example fresh cheese, soft cheese, hard cheese, milk beverages, whey, butter, products containing partially or fully hydrolysed milk protein), products of soya protein or other soya bean fractions (for example soya milk and products made therefrom, preparations containing soya lecithin, fermented products such as tofu or tempe or products made therefrom, soya sauces), vegetable preparations (for example ketchup, sauces, dried vegetables, deep-frozen vegetables, precooked vegetables, vegetables stored in vinegar, vegetable concentrates or pastes, preserved vegetables, potato preparations), snack articles (for example baked or fried potato chips or potato dough products, bread dough products, extrudates based on corner, rice or groundnut), fat- and oil-based products or emulsions thereof (for example mayonnaise, spread, remoulade, dressings, spice preparations), other ready meals and soups (for example dried soups, instant soups, precooked soups), sauces (instant sauces, dried sauces, ready sauces), spices or spice preparations (for example mustard preparations, horseradish preparations), seasoning mixtures and in particular condiments (seasonings) which are used for example in the snack sector.

Particularly preferred are preparations (preferably with a reduced sodium glutamate content) used for staple or luxury food, for example bakery items (for example bread, biscuits, cakes, other pastries), vegetable juice preparations, meat products (for example ham, fresh sausage of raw sausage preparations, spiced or marinated fresh or salt meat products), spiced or marinated fish products (for example surimi), eggs or egg products (dried egg, egg white, egg yolk), cereal products (for example precooked ready rice products, rice flour products, raw or precooked noodles and pasta products), milk products (for example fresh cheese, soft cheese, hard cheese, milk beverages, whey, butter, products containing partially or fully hydrolysed milk protein), products of soya protein or other soya bean fractions (for example soya milk and products made therefrom, preparations containing soya lecithin, fermented products such as tofu or tempe or products made therefrom, soya sauces), fish sauces, for example anchovy sauces, oyster sauces, vegetable preparations (for example ketchup, sauces, dried vegetables, deep-frozen vegetables, precooked vegetables, vegetables stored in vinegar, vegetable concentrates or pastes, preserved vegetables, potato preparations), snack articles (for example baked or fried potato chips or potato dough products, bread dough products, extrudates based on corner, rice or groundnut), fat- and oil-based products or emulsions thereof (for example mayonnaise, spread, remoulade, dressings, spice preparations), ready meals, soups (for example dried soups, instant soups, precooked soups), stock cubes, sauces (instant sauces, dried sauces, ready sauces), herbs, spices, seasonings, spice mixtures, in particular condiments (seasonings) which are used for example in the snack sector.

The preparations in the sense of the invention may also be provided in the form of capsules, tablets (uncoated and coated tablets, for example gastric juice-resistant coatings), lozenges, granules, pellets, solid mixtures, dispersions in liquid phases, as emulsions, as powders, and solutions, as pastes or as other swallowable or chewable preparations, for example as food supplements.

The semifinished products according to the invention are generally used to produce preparations ready for use or consumption used in staple or luxury food.

In particular, semifinished products according to the invention may be used for additive enhancement of the umami flavor of sodium glutamate-reduced staple and luxury foods, and also directly as seasonings for the industrial or nonindustrial preparation of staple and/or luxury foods.

Semifinished products according to the invention preferably contain:
  a total amount of from 10 ppm to 100000 ppm (preferentially up to 800 ppm), preferably 25 ppm to 5000 ppm (preferentially up to 750 ppm), in particular 50 ppm to 1200 ppm (preferentially up to 700 ppm), compounds of the formulae (I) and (ent-I) or—when using the mixtures defined above—compounds of the formulae (I), (ent-I), (II), (ent-II), (III), (ent-III), (IV), (ent-IV),
  no sodium glutamate or a proportion of from 0.00001 to 10 wt. %, preferably 0.0001 to 5 wt. %, in particular 0.001 wt. % to 2 wt. % of sodium glutamate,
  and optionally a proportion of from 0.0001 wt. % to 90 wt. %, preferably 0.001 wt. % to 30 wt. % of an aroma composition, respectively expressed in terms of the total weight of the semifinished product.

The compositions, preparations or semifinished products according to the invention are preferably produced by dissolving and mixing the compounds of formulae (I) and (ent-I) or mixtures defined above in mixtures of ethanol and optionally demineralized and/or purified water; the solutions are subsequently converted by a drying process, preferably a spray-drying, vacuum freeze-drying, reverse-osmosis, evaporation or other concentration process, or a combination of the said processes, into an (at least almost) dry preparation. The drying may be carried out with the aid of excipients (for example starches, starch derivatives, maltodextrin, silica gel, see above) or auxiliaries (for example plant gums, stabilizers). The drying is preferably carried out by means of spray drying or vacuum freeze drying.

Preferred compositions, preparations or semifinished products according to the invention are spices, spice mixtures, seasonings, stock cubes, instant soups, instant sauces, vegetarian ready meals, ready meals containing meat, fish sauces such as for example anchovy sauces, oyster sauces and soya sauces.

According to another preferred embodiment, in order to produce compositions, preparations or semifinished products according to the invention, compounds of the formulae (I) and (ent-I) or mixtures as defined above, and optionally other constituents, are first incorporated into emulsions, liposomes (for example based on phosphatidylcholine), microspheres, nanospheres or into capsules, granules or extrudates of a matrix suitable for staple and luxury food (for example made of starch, starch derivatives, cellulose or cellulose derivatives such as hydroxypropyl cellulose, other polysaccharides such as alginate, natural fats, natural waxes such as beeswax or carnauba wax, or proteins such as gelatines).

In another preferred production method, compounds of the formulae (I) and (ent-I) or mixtures as defined above are complexed with one or more suitable sequestrants, for example with cyclodextrins or cyclodextrin derivatives, preferably alpha- or beta-cyclodextrin, and used in this complexed form.

Preparations according to the invention are particularly preferred when the matrix is selected so that the compounds of formulae (I) and (ent-I) or mixtures as defined above are released from the matrix in a delayed fashion, so that a long-lasting effect is obtained. Here, for example, natural fats, natural waxes (for example beeswax or carnauba wax) or natural ballasts (wheat fibres, apple fibres, owed fibres, orange fibres) may be used as a matrix.

Other constituents of a preparation ready for consumption or semifinished product according to the invention, used for staple or luxury food, may be customary base materials, auxiliaries and additives for staple or luxury food, for example water, mixtures of fresh or processed plant or animal basic or raw materials (for example raw, baked, dried, fermented, smoked and/or cooked meat, bones, cartilage, fish, vegetables, herbs, nuts, vegetable juices or pastes or mixtures thereof), digestible or indigestible carbohydrates (for example saccharoses, maltoses, fructoses, glucoses, dextrins, amyloses, amylopectins, inulins, xylanes, celluloses, tagatoses), sugar alcohols (for example sorbite, erythritol), natural of hardened facts (for example tallow, lard, palm fat, cocoa fat, hardened plane fat), oils (for example sunflower oil, groundnut oil, corn seed oil, olive oil, fish oil, soya oil, sesame oil), fatty acids or salts thereof (for example potassium stearate), proteinogenic or non-proteinogenic amino acids and related compounds (for example γ-aminobutyric acid, taurine), peptides (for example glutathione), native or processed proteins (for example gelatines), enzymes (for example peptidases, nucleic acids, nucleotides, flavor correctors for unpleasant flavor impressions, further flavor modulators for other generally unpleasant flavor impressions, other flavor-modulating substances (for example inositol phosphate, nucleotides such as guanosine monophosphate, adenosine monophosphate or other substances such as sodium glutamate or 2-phenoxypropionic acid), emulsifiers (for example lecithins, diacylglycerols, gum arabic), stabilizers (for example carrageenan, alginate), preservatives (for example benzoic acid and salts thereof, sorbic acid and salts thereof), antioxidants (for example tocopherol, ascorbic acid), chelators (for example citric acid), organic or inorganic acidifiers (for example acetic acid, phosphoric acid), additional bitters (for example quinine, caffeine, limonin, amarogentin, humolone, lupolone, catechine, tannins), substances preventing enzymatic browning (for example sulfite, ascorbic acid), essential oils, plant extracts, natural or synthetic dyes or pigments (for example carotinoids, flavonoids, anthocyans, chlorophyll and derivatives thereof), spices, trigeminally active substances or plant extracts containing such trigeminally active substances, synthetic, natural or naturally identical aromatizers or fragrances and odor correctors.

Compositions, preparations or semifinished products according to the invention preferably contain an aroma composition in order to round or refined the flavor and/or the odor. A composition according to the invention, which contains a solid excipient and an aroma composition as further constituents, has already been described above. Suitable aroma compositions contain for example synthetic, natural or naturally identical aromatizers. Fragrances and flavor materials, reaction aromas, fragrance aromas or other preparations giving an aroma (for example protein [semi]hydrolysates, grill aromas, plant extracts, spices, spice preparations, vegetables and/or vessel will preparations) as well as suitable auxiliaries and excipients. In particular, here the aroma compositions not according to the invention or their constituents which cause a roasted, meaty (in particular chicken, fish, seafood, beef, pork, lamb, mutton, goat), vegetable (in particular tomato, onion, garlic, celery, leek, mushroom, egg plant, seaweed), a savory (in particular black and white pepper, chilli, paprika, cardamom, nutmeg, pimento, mustard and mustard products), roasted, yeasty, boiled, fatty, salty and/or pungent aroma impression, and can therefore enhance the savory impression, are suitable. In general, the aroma compositions contain more than one of the said ingredients.

In another configuration of the present invention, compounds of the formulae (I) and (ent-I) or mixtures as defined above are used in compositions, preparations and semifinished products in combination with at least one further substance, not per se according to the invention, former skin or reducing an unpleasant (bitter, metallic, limy, acid, astringent) flavor impressions or for enhancing or producing a pleasant flavor impressions (sweet, salty, umami).

In this way, it is possible to achieve an enhancement of the flavor, in particular the umami flavor. These further substances may be selected from the following list, without thereby limiting the invention: monosodium glutamate, glutamic acid, nucleotides (for example adenosine-5'-monophosphate, cytidine-5'-monophosphate, inosine-5'-monophosphate, guanosine-5'-monophosphate) or their pharmaceutically acceptable salts, lactisols, hydroxyflavanones (for example eriodictyol, homoeriodictyol or their sodium salts), in particular according to EP 1 258 200, hydroxybenzoic acid amides (for example 2,4-dihydroxybenzoic acid vanillylamide, 4-dihydroxybenzoic acid vanillylamide), mixtures of whey proteins with lecithins, yeast extracts, plant hydrolysates, powdered vegetables (for example onion powder, tomato powder), plant extracts (for example of lovage or mushrooms such as shitake), see algae and inorganic salt mixtures.

In a preferred configuration of the present invention, the compounds of formula (I) and/or (ent-I) to be used according to the invention are used in the compositions, preparations and semifinished products according to the invention in combination with at least one sweetness-enhancing substance, in particular with one or more compounds according to WO 2007/014879 A1 or WO 2007/107596 A1, especially together with hesperetin and/or phloretin. An enhancement and deepening as well as rounding of the flavor profile are thereby achieved, particularly in compositions, preparations and semifinished products with a savory and/or salty flavor. The total proportion of hesperetin and/or phloretin in such a compositions or preparations preferably lies in the range of from 1 to 400 ppm, preferably in the range of 5-200 ppm, expressed in terms of the total weight of the composition or preparation.

In addition to one or more sweetness-enhancing substances, the compositions, preparations and semifinished products according to the invention may furthermore contain flavor materials which cause a trigeminal stimulus (tingling, tickling, pungent, cooling etc.). For instance, in the combination of the compounds of formula (I) and/or (ent-I) to be used according to the invention, a further improved flavor profile preferred by consumers is achieved with hesperetin and/or phloretin on the one hand, and cis- and/or trans-pellitorin on the other hand (see WO 2004/000787 or WO 2004/043906). The total proportion of cis- and/or trans-pellitorin in such compositions or preparations preferably lies in the range of from 0.5 to 500 ppm, preferably in the range of 5-100 ppm, expressed in terms of the total weight of the composition or preparation.

Modulating aroma and/or flavor materials are preferably selected from the group consisting of adenosine-5'-monophosphate, cytidine-5'-monophosphate, inosine-5'-monophosphate, and their pharmaceutically acceptable salts; lactisoles; 2,4-dihydroxybenzoic acid; 3-hydroxybenzoic acid; sodium salts, preferably sodium-chloride, sodium lactate, sodium citrate, sodium acetate, sodium gluconate; hydroxyflavanones, for example eriodictyol, homoeriodictyol, and their sodium salts; hydroxybenzoic acid amides, for example 2,4-dihydroxybenzoic acid vanillylamide, 2,4-dihydroxybenzoic acid-N-(4-hydroxy-3-methoxybenzyl)amide, 2,4,6-trihydroxybenzoic acid-N-(4-hydroxy-3-methoxybenzyl) amide, 2-hydroxy-benzoic acid-N-4-(hydroxy-3-methoxybenzyl)amide, 4-hydroxybenzoic acid-N-(4-hydroxy-3-methoxybenzyl)-amide, 2,4-dihydroxybenzoic acid-N-(4-hydroxy-3-methoxybenzyl)amide monosodium salt, 2,4-dihydroxybenzoic acid-N-2-(4-hydroxy-3-methoxyphenyl)-ethyl amide, 2,4-dihydroxybenzoic acid-N-(4-hydroxy-3-ethoxybenzyl)amide, 2,4-dihydroxybenzoic acid-N-(3,4-dihydroxybenzyl)amide and 2-hydroxy-5-methoxy-N-[2-(4-hydroxy-3-methoxyphenyl)ethyl]amide; 4-hydroxybenzoic acid vanillylamide (in particular such as described in WO 2006/024587, which by way of reference is part of this application with respect to the corresponding compounds disclosed therein); hydroxydeoxybenzoins, for example 2-(4-hydroxy-3-methoxyphenyl)-1-(2,4,6-trihydroxyphenyl)ethanone, 1-(2,4-dihydroxyphenyl)-2-(4-hydroxy-3-methoxy-phenyl)ethanone, 1-(2-hydroxy-4-methoxyphenyl)-2-(4-hydroxy-3-methoxy-phenyl)ethanone) (in particular such as described in WO 2006/106023, which by way of reference is part of this application with respect to the corresponding compounds disclosed therein); hydroxyphenylalkane diones, for example gingerdione-[2], gingerdione-[3], gingerdione-[4], dehydrogingerdione-[2], dehydrogingerdione-[3], dehydrogingerdione-[4]) (in particular such as described in WO 2007/003527, which by way of reference is part of this application with respect to the corresponding compounds disclosed therein); diacetyl trimers (in particular such as described in WO 2006/058893, which by way of reference is part of this application with respect to the corresponding compounds disclosed therein); γ-aminobutyric acids (in particular such as described in WO 2005/096841, which by way of reference is part of this application with respect to the corresponding compounds disclosed therein) and divanillins (in particular divanillin as described in WO 2004/078302, which by way of reference is part of this application with respect to the corresponding compounds disclosed therein); bicyclo[4.1.0]heptane-7-carboxylic acid amides, in particular such as described in PCT/EP2007/061171 and the documents based thereon (Symrise), which by way of reference is part of this application with respect to the corresponding compounds disclosed therein; cyclopropanecarboxylic acid (3-methyl-cyclo-hexyl)amides, in particular such as described in U.S. Provisional 60/916,589 of May 8, 2007 and the documents based thereon (Symrise), which by way of reference is part of this application with respect to the corresponding compounds disclosed therein; aromatic neo-menthylamides, in particular such as described in U.S. Provisional Application 60/984,023 of Oct. 31, 2007 and the documents based thereon (Symrise), which by way of reference is part of this application with respect to the corresponding compounds disclosed therein.

According to another configuration of the invention, a composition, preparation ready for use or consumption or semifinished product according to the invention respectively as described above comprises in particular one or more sweetness-enhancing substances. In particular, the compounds according to the invention of formulae (I) or (II) or the mixtures according to the invention (as described above) are in this case used in combination with at least one sweetness-enhancing substance, in particular with one or more compounds according to WO 2007/014879 A1 or WO 2007/107596 A1, especially together with hesperetin and/or phloretin. An enhancement and deepening as well as rounding of the flavor profile are thereby achieved, in particular of the savory and/or salty flavor of the composition, preparation or semifinished product. For semifinished products, the total proportion of hesperetin and/or phloretin then preferably lies in the range of from 10 to 100000 ppm, expressed in terms of the total weight of the semifinished product, while in food ready for consumption in the total proportion of hesperetin and/or phloretin expressed in terms of the total weight of the food then preferably lies in the range of from 1 to 400 ppm, preferably in the range of from 5 to 200 ppm.

Preferably, the compositions, preparations or semifinished products according to the invention also contain one or more sweetness-enhancing substances and/or one or more materials which cause a trigeminal stimulus (tingling, tickling, pungent, cooling etc.). In particular when the compounds of formulae (I) or (II) according to the invention or the corresponding mixtures according to the invention are combined with hesperetin and/or phloretin but also with cis- and/or trans-pellitorin (see WO 2004/000787 or WO 2004/043906), a further improved flavor profile preferred by consumers is achieved. The total proportion of cis- and/or trans-pellitorin in these compositions or preparations or semifinished products then preferably lies in the range of from 0.1 to 500 ppm, preferably in the range of 5 to 100 ppm, expressed in terms of the total weight of the composition, preparation or semifinished product.

The preceding text reveals that another aspect of the present invention also relates to a method for producing, imparting, modifying and/or enhancing a flavor, in particular an umami flavor, in a (i) preparation ready for use or consumption or (ii) semifinished product used in staple foods, oral care or luxury foods. Such a method according to the invention comprises the following step:

mixing an active flavoring amount of or more compounds of the formulae (I) and (ent-I) or mixtures defined above or a composition according to the invention with one or more further constituents of the (i) preparation ready for consumption or use or (ii) semifinished product, or applying an active flavoring amount of or more compounds of the formulae (I) and (ent-I) or mixtures defined above or a composition according to the invention to one or more further constituents of the (i) preparation ready for consumption or use or (ii) semifinished product, or embedding an active flavoring amount of or more compounds of the formulae (I) and (ent-I) or mixtures defined above or a composition according to the invention in a shell or matrix material.

In respect of preferred compounds and mixtures, that stated above applies accordingly.

Other aspects of the invention may be found in the following examples and the appended claims.

EXAMPLES

The following examples explain the invention. Unless otherwise indicated, all data refer to weight.

The neo-menthylamines required as starting material are prepared according to a protocol of Wallach et al. (*Ann. Chem.* 1893, 276, 296-313) from the corresponding menthones in a purity ≥90%, preferably ≥95%. A mixture of all possible isomeric menthylamines can be obtained according to the aforementioned protocol without corresponding crystallization of the menthylformamide (an intermediate product) in a purity of 99.3% (24.1% menthyl-amine, 55.5% neo-menthylamine, 2.4% iso-menthylamine, 17.3% neo-iso-menthylamine). In this case, both pure-enantiomer D- and L-menthones and a racemic D/L-menthone mixture may be employed. All menthones used may be mixed with up to 25% of the corresponding iso-menthones. The diastereomer-enriched neo-menthylamines may likewise be obtained in a purity of ≥60%, preferably ≥90%, particularly preferably ≥95% under optimized conditions by fractional crystallization of the corresponding formamides.

The neo-mentholes required are commercially available both as a racemate and as pure enantiomers.

The flavor profiles were determined by a trained panel of at least 5 testers by tasting against a 0.5% strength salt and a 0.5% strength sugar solution General Working Protocol (GWP 1): Reaction of Neo-Menthol with Triphosgene and Primary Amines to Form the Corresponding Carbamates A solution of 0.8 g (2.6 mmol) triphosgene in 10 ml dichloromethane is slowly added dropwise to a solution of 1.0 g (6.4 mmol) of the corresponding neo-menthol (D, L or racemic) and 0.7 g (8.4 mmol) pyridine in 30 ml dichloromethane cooled to 0° C. The solution is stirred for 1 h at 0° C., before another 1.0 ml (12.4 mmol) pyridine and 10.2 mmol of the corresponding amine are added. After further stirring for 4 h at 0° C., 35 ml of 1 M hydrochloric acid are added and the aqueous phase is extracted three times with 40 ml dichloromethane each. The combined organic phases are washed with saturated sodium chloride solution, dried over sodium sulfate and freed from the solvent in a rotary evaporator. The purification is carried out by chromatography with various mixtures of pentane and diethyl ether on silica gel.

General Working Protocol (GWP 2): Reaction of Neo-Menthylamine with Triphosgene to Form the Corresponding Isocyanates A solution of 25.9 g (166.7 mmol) of the corresponding neo-menthylamine (D, L or racemic) in 75 ml dichloromethane is added under a protective gas to a solution of 15.0 g (50.5 mmol) triphosgene in 200 ml dichloromethane cooled to 0° C., so slowly that the internal temperature does not exceed 5° C. It is subsequently stirred for three hours at 0° C. and a further 14 hours at room temperature. The reaction mixture is diluted with 100 ml dichloromethane and washed two times with 150 ml iced water and two times with 150 ml $NaHCO_3$ solution. The organic phase is concentrated in a rotary evaporator and the desired product is obtained by silica gel chromatography with pentane/diethyl ether (10:1).

General Working Protocol (GWP 3): Reaction of Neo-Menthylamine with Carbon Disulfide to Form the Corresponding Isocyanates 7.1 g (93.2 mmol) carbon disulfide are added under a protective gas to a solution of 14.5 g (93.4 mmol) of the corresponding neo-menthylamine (D, L or racemic) and 9.4 g (92.9 mmol) triethylamine in 150 ml cyclohexane cooled to 0° C., so slowly that the internal temperature does not exceed 5° C. It is subsequently stirred for three hours at 0° C., and the resulting solid is filtered off and washed four times with 25 ml diethyl ether each. The solid is finally dissolved in 150 ml dichloromethane, a further 9.4 g (92.9 mmol) triethylamine are added, it is cooled to 0° C. and 10.1 g (93.1 mmol) ethyl chloroformate are added so slowly that the internal temperature does not exceed 5° C. It is subsequently first re-stirred for 30 min at 0° C. before the reaction mixture is refluxed with evolution of $CO_2$ for 2 hours. After the end of the gas evolution, the organic phase is washed successively each with 50 ml water, 10% strength hydrochloric acid, water and saturated $NaHCO_3$ solution. The organic phase is dried over sodium sulfate and, after removing the solvent, the residue is filtered over 40 g silica gel and re-washed with 350 ml pentane. After again removing the solvent, the desired thioisocyanate is obtained which may be contaminated with up to 25% of the corresponding isocyanate.

General Working Protocol (GWP 4): Reaction of Isocyanates Neo-Menthyl-Amine Isocyanate or Neo-Menthylamine Isothiocyanate with Primary Amines to Form the Corresponding Ureas or Thioureas 2.5 equivalents of the corresponding amine are added to a solution of the corresponding neo-menthylisocyanate or neo-menthylisothiocyanate prepared according to GWP 2 or GWP 3 in heptane or toluene, and the reaction solution is subsequently refluxed for six hours. After cooling to room temperature, it is dilated with dichloromethane or toluene and the organic phase is washed with 10% strength hydrochloric acid, water and saturated $NaHCO_3$ solution. The organic phases then dried over sodium sulfate, the solvent is removed in a rotary evaporator and the raw product is purified by silica gel chromatography and/or crystallization.

Synthesis Example 1

1-((1S,2S,5R)-2-Isopropyl-5-methyl-cyclohexyl)-3-(3-methoxy-propyl)-urea (1)/1-((1R,2R,5S)-2-isopropyl-5-methyl-cyclohexyl)-3-(3-methoxy-propyl)-urea (2)

As described in GWP 4, the racemic neo-menthyl isocyanate prepared according to GWP 2 is reacted with 3-methoxypropylamine to form the desired products.

Analytical Data:

$^1$H-NMR (400 MHz, $CDCl_3$): 0.87 (d, J=6.5 Hz, 3H); 0.87-0.95 (m, 1H); 0.89 (d, J=6.6 Hz, 3H); 0.91 (d, J=6.6 Hz, 3H); 0.97-1.06 (m, 1H); 1.39 (m, 1H); 1.48 (m, 1H); 1.28-1.41 (m, 3H); 1.71 (m, 1H); 1.77 (m, 2H); 1.86 (m, 2H); 3.28 (dt, J=5.6 Hz/J=6.3 Hz, 2H); 3.34 (s, 3H); 3.48 (m, 2H); 4.02 (bs, 1H); 4.43 (bd, J=8.9 Hz, 1H); 4.73 (bs, 1H) ppm.

$^{13}$C-NMR (100 MHz, $CDCl_3$): 20.8 ($CH_3$); 21.0 ($CH_3$); 22.3 ($CH_3$); 25.3 ($CH_2$); 26.7 (CH); 29.5 (CH); 29.8 ($CH_2$); 34.8 ($CH_2$); 38.9 ($CH_2$); 40.7 ($CH_2$); 46.7 (CH); 47.1 (CH); 58.7 ($CH_3$); 71.4 ($CH_2$); 157.8 (C=O) ppm.

Mass Spectrum (EI): m/z (%)=270 (M·+, 11); 227 (14); 133 (16); 112 (25); 90 (26); 70 (100); 56 (14); 43 (16); 41 (16); 30 (19).

Flavor Profile: sweet, salty, metallic, umami.

Synthesis Example 1a 1-((1S,2S,5R)-2-Isopropyl-5-methyl-cyclohexyl)-3-(3-methoxy-propyl)-urea (1)

Similarly to GWP 4, the (1S,2S,5R)-neo-menthyl isocyanate prepared according to GWP 2 is reacted with 3-methoxypropylamine to form the desired pure-enantiomer product.

Analytical Data:

NMR and MS: cf. Synthesis Example 1

Flavor Profile: salty, long-lasting, umami, no by notes.

Synthesis Example 2

1-(3-Hydroxy-propyl)-3-((1S,2S,5R)-2-isopropyl-5-methyl-cyclohexyl)-urea (3)/1-(3-Hydroxy-propyl)-3-((1R,2R,5S)-2-isopropyl-5-methyl-cyclohexyl)-urea (4)

As described in GWP 4, the racemic neo-menthyl isocyanate prepared according to GWP 2 is reacted with 3-aminopropan-1-ol to form the desired products.

Analytical Data:

$^1$H-NMR (400 MHz, CDCl$_3$): 0.87 (d, J=6.5 Hz, 3H); 0.89 (d, J=6.7 Hz, 3H); 0.91 (d, J=6.7 Hz, 3H); 1.00 (m, 3H); 1.38 (m, 1H); 1.47 (m, 1H); 1.55 (m, 1H); 1.64 (m, 2H); 1.71 (m, 1H); 1.82 (m, 2H); 3.32 (m, 1H); 3.38 (m, 1H); 3.64 (qart, J=5.8 Hz, 2H); 3.96 (bt, J=6.3 Hz, 1H); 4.07 (bd, J=7.3 Hz, 1H); 4.85 (bd, J=9.1 Hz, 1H); 5.05 (bt, J=6.2 Hz, 1H) ppm.

$^{13}$C-NMR (100 MHz, CDCl$_3$): 20.8 (CH$_3$); 21.0 (CH$_3$); 22.3 (CH$_3$); 25.3 (CH$_2$); 26.7 (CH); 29.6 (CH); 33.3 (CH$_2$); 34.8 (CH$_2$); 36.4 (CH$_2$); 40.8 (CH$_2$); 46.6 (CH); 47.0 (CH); 58.9 (CH$_2$); 159.1 (C=O) ppm.

Mass Spectrum (LC-MS: Luna C18; 150×2 mm; 0.2 ml/min; H$_2$O/CH$_3$CN 95/5→0/100): m/z (%)=514 (18); 513 (100); 413 (4); 412 (4); 259 (3) 258 (2).

Flavor Profile: fishy, salty, weakly umami.

Synthesis Example 3

1-((1S,2S,5R)-2-Isopropyl-5-methyl-cyclohexyl)-3-(2-methoxy-1-methyl-ethyl)-urea (5)/1-((1R,2R,5S)-2-isopropyl-5-methyl-cyclohexyl)-3-(2-methoxy-1-methyl-ethyl)-urea (6)

As described in GWP 4, the racemic neo-menthyl isocyanate prepared according to GWP 2 is reacted with 2-methoxy-1-methyl-ethylamine to form the desired products.

Analytical Data (2 Diastereomers):

$^{13}$C-NMR (100 MHz, CDCl$_3$): 18.20, 18.29 (CH$_3$); 20.91, 20.94 (CH$_3$); 21.0 (CH$_3$); 22.37, 22.40 (CH$_3$); 25.25, 25.32 (CH$_2$); 26.66, 26.68 (CH); 29.34, 29.52 (CH); 35.0 (CH$_2$); 40.79, 40.94 (CH$_2$); 46.31, 46.54 (CH); 47.72, 46.76 (CH); 46.8 (CH); 58.96, 59.00 (CH$_3$); 77.56, 77.90 (CH$_2$); 158.07, 158.28 (C=O) ppm.

Mass Spectrum (EI): m/z (%)=270 (M·+, 14); 225 (13); 112 (8); 90 (9); 70 (22); 69 (9); 57 (8); 55 (7); 44 (100); 43 (28).

Flavor Profile: long-lasting, salty, umami.

Synthesis Example 4

3-[3-((1S,2S,5R)-2-Isopropyl-5-methyl-cyclohexyl)-ureido]-butyric acid ethyl ester (7)/3-[3-((1R,2R,5S)-2-isopropyl-5-methyl-cyclohexyl)-ureido]-butyric acid ethyl ester (8)

As described in GWP 4, the racemic neo-menthyl isocyanate prepared according to GWP 2 is reacted with ethyl 3-aminobutyrate to form the desired products.

Analytical Data (2 Diastereomers):

$^{13}$C-NMR (100 MHz, CDCl$_3$): 14.2 (CH$_3$); 20.82, 20.83 (CH$_3$); 20.85, 20.93 (CH$_3$); 21.0 (CH$_3$); 22.3 (CH$_3$); 25.26, 25.28 (CH$_2$); 26.65, 26.69 (CH); 29.45, 29.52 (CH); 34.84, 34.86 (CH$_2$); 40.73, 40.74 (CH$_2$); 40.95, 41.05 (CH$_2$); 43.16, 43.27 (CH); 46.67, 46.68 (CH); 47.0 (CH); 60.53, 60.55 (CH$_2$); 156.96, 157.03 (C=O); 172.32, 172.35 (C=O) ppm.

Mass Spectrum (EI): m/z (%)=312 (M·+, 9); 267 (10); 132 (44); 130 (11); 112 (22); 70 (100); 55 (11); 44 (38); 43 (17); 41 (13).

Flavor Profile: bitter, salty, metallic, umami.

Synthesis Example 5

(3-Methoxy-propyl)-carbamic acid (1S,2S,5R)-2-isopropyl-5-methyl-cyclohexyl ester (9) and (3-methoxy-propyl)-carbamic acid (1R,2R,5S)-2-isopropyl-5-methyl-cyclohexyl ester (10)

As described in GWP 1, racemic neo-menthyl is reacted with 3-methoxypropylamine to form the desired products.

Analytical Data:

$^1$H-NMR (400 MHz, CDCl$_3$): 0.84-1.07 (m, 3H); 0.85 (d, J=6.4 Hz, 3H); 0.89 (d, J=6.6 Hz, 3H); 0.90 (d, J=6.5 Hz, 3H); 1.25 (m, 1H); 1.46 (m, 1H); 1.56-1.81 (m, 5H); 1.97 (bd, J=13.6 Hz, 1H); 3.28 (m, 2H); 3.34 (s, 3H); 3.43 (t, J=6.0 Hz, 2H); 4.90 (bs, 1H); 5.07 (bs, 1H) ppm.

$^{13}$C-NMR (100 MHz, CDCl$_3$): 20.87 (CH$_3$); 20.92 (CH$_3$); 22.3 (CH$_3$); 25.0 (CH$_2$); 26.5 (CH); 29.3 (CH); 29.7 (CH$_2$); 34.9 (CH$_2$); 38.9 (CH$_2$); 39.6 (CH$_2$); 46.9 (CH); 58.7 (CH$_3$); 71.1 (CH$_2$); 71.3 (CH); 156.5 (C=O) ppm.

Mass Spectrum (EI): m/z (%)=271 (M·+, 1); 133 (51); 95 (97); 90 (90); 83 (100); 81 (65); 71 (58); 69 (54); 55 (61); 41 (53).

Flavor Profile: sweet, salty, umami, slightly bitter.

Synthesis Example 5A (3-Methoxy-propyl)-carbamic acid (1S,2S,5R)-2-isopropyl-5-methyl-cyclohexyl ester (9)

As described in GWP 1, (1S,2S,5R)-neo-menthol is reacted with 3-methoxypropylamine to form the desired products.

Analytical Data:

NMR and MS: cf. Synthesis Example 5

Flavor Profile: umami, salty, metallic, bitter.

Synthesis Example 5B (3-Methoxy-propyl)-carbamic acid (1R,2R,5S)-2-isopropyl-5-methyl-cyclohexyl ester (10)

As described in GWP 1, (1R,2R,5S)-neo-menthol is reacted with 3-methoxypropylamine to form the desired products.

Analytical Data:
NMR and MS: cf. Synthesis Example 5
Flavor Profile: umami, salty, metallic, not bitter

Synthesis Example 6

4-((1S,2S,5R)-2-Isopropyl-5-methyl-cyclohexyloxycarbonylamino)-butyric acid ethyl ester (11)/4-((1R,2R,5S)-2-isopropyl-5-methyl-cyclohexyloxycarbonylamino)-butyric acid ethyl ester (12)

As described in GWP 1, racemic neo-menthol is reacted with 3-methoxypropylamine to form the desired products.
Analytical Data:
$^1$H-NMR (400 MHz, CDCl$_3$): 0.84-1.07 (m, 3H); 0.85 (d, J=6.6 Hz, 3H); 0.88 (d, J=6.6 Hz, 3H); 0.89 (d, J=6.6 Hz, 3H); 1.23-1.33 (m, 1H); 1.26 (t, J=7.2 Hz, 3H); 1.45 (m, 1H); 1.50-1.77 (m, 3H); 1.84 (quint, J=7.1 Hz, 2H); 1.97 (m, 1H); 2.35 (t, J=7.3 Hz, 2H); 3.22 (m, 2H); 4.13 (quart, J=7.2 Hz, 2H); 4.78 (bs, 1H); 5.07 (bs, 1H) ppm.
$^{13}$C-NMR (100 MHz, CDCl$_3$): 14.2 (CH$_3$); 20.85 (CH$_3$); 20.92 (CH$_3$); 22.2 (CH$_3$); 25.0 (CH$_2$); 25.3 (CH$_2$); 26.5 (CH); 29.3 (CH); 31.6 (CH$_2$); 34.9 (CH$_2$); 40.3 (CH$_2$); 46.9 (CH); 60.5 (CH$_2$); 71.4 (CH); 156.5 (C=O); 173.3 (C=O) ppm.
Mass Spectrum (EI): m/z (%)=175 (76); 130 (84); 112 (56); 95 (90); 86 (59); 83 (100); 81 (62); 69 (66); 55 (59); 44 (74).
Flavor Profile: bitter, salty, umami.

Synthesis Example 6A 4-((1S,2S,5R)-2-Isopropyl-5-methyl-cyclohexyloxycarbonylamino)-butyric acid ethyl ester (11)

As described in GWP 1, (1S,2S,5R)-neo-menthol is reacted with 3-methoxypropylamine to form the desired products.
Analytical Data:
NMR and MS: cf. Synthesis Example 6
Flavor Profile: salty, umami, relatively weak in comparison with the racemate.

Synthesis Example 6B 4-((1R,2R,5S)-2-Isopropyl-5-methyl-cyclohexyloxycarbonylamino)-butyric acid ethyl ester (12)

As described in GWP 1, (1R,2R,5S)-neo-menthol is reacted with 3-methoxypropylamine to form the desired products.
Analytical Data:
NMR and MS: cf. Synthesis Example 6
Flavor Profile: salty, umami, delayed and weaker in comparison with the racemate.

The following structures are further examples from this substance class, which were prepared according to GWP 1-GWP 4—starting from racemic neo-menthol or neo-menthylamine—and tasted.
[racemisch=racemic]

| Structure | MS Data | Flavor Profile |
| --- | --- | --- |
| racemic | m/z (%) = 227 (M$^{•+}$, 0.2); 123 (26); 113 (24); 95 (100); 83 (37); 81 (56); 71 (31); 69 (29); 55 (34); 41 (32). | cooling, umami, menthol note |
| racemic | m/z (%) = 257 (M$^{•+}$, 0.1); 138 (56); 120 (49); 95 (100); 83 (72); 81 (69); 76 (84); 69 (42); 55 (59); 41 (46). | soapy, vegetable, asparagus, potato, mouthfeel, slightly umami |
| racemic | m/z (%) = 257 (M$^{•+}$, 0.4); 119 (41); 95 (46); 87 (31); 83 (100); 81 (38); 69 (37); 57 (31); 55 (43); 30 (30). | sweet, umami |

-continued

| Structure | MS Data | Flavor Profile |
|---|---|---|
| [menthyl-NH-C(O)-NH-CH2CH2-OCH3], racemic | m/z (%) = 256 (M•+, 13); 171 (15); 112 (16); 76 (36); 70 (100); 55 (16); 44 (21); 43 (36); 41 (15); 30 (74). | fishy, salty, umami |
| [menthyl-O-C(O)-NH-CH2CH2CH2-OCH2CH3], racemic | m/z (%) = 285 (M•+, 0.4); 104 (65); 103 (43); 102 (82); 101 (49); 95 (74); 83 (100); 81 (50); 57 (53); 55 (49). | rancid, musty, bitter, umami |
| [menthyl-NH-C(O)-NH-CH2CH2-O-CH2CH2-OH], racemic | m/z (%) (LC-MS) = 573 (100); 444 (4); 445 (5); 290 (12); 289 (19). | fatty, oily (fish), umami |
| [menthyl-NH-C(O)-NH-CH2CH2CH2-O-CH2CH3], racemic | m/z (%) = 284 (M•+, 12); 112 (17); 104 (22); 74 (12); 70 (100); 56 (15); 44 (11); 43 (14); 41 (16); 30 (33). | fatty, tallow, dry-dusty, long-lasting, umami |
| [menthyl-NH-C(O)-NH-CH2CH2-OH], racemic | m/z (%) (LC-MS) = 486 (2); 485 (100); 400 (2); 399 (3); 398 (2); 397 (2); 245 (2). | alga, roasted note, umami, sweet |
| [menthyl-O-C(O)-NH-CH2CH2-O-CH2CH2-OH], racemic | m/z (%) = 119 (33); 95 (38); 88 (46); 83 (100); 81 (33); 69 (38); 57 (29); 55 (39); 44 (33); 43 (34). | fatty, tallow, oily, salty, metallic |

-continued
| Structure | MS Data | Flavor Profile |
|---|---|---|
| 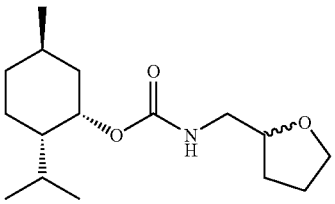 racemic | m/z (%) = 139 (21); 102 (16); 95 (12); 83 (40); 81 (13); 71 (100); 57 (14); 55 (19); 43 (20); 41 (14). | bitter, long-lasting, umami |
| 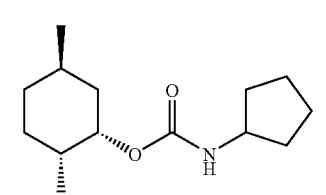 racemic | m/z (%) = 267 (M•+, 0.3); 138 (63); 130 (100); 95 (59); 83 (85); 81 (46); 69 (50); 56 (30); 55 (45); 41 (33). | bitter, salty |
| 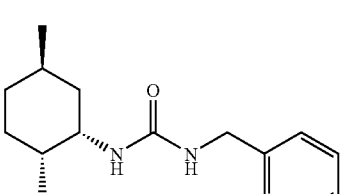 racemic | m/z (%) = 288 (M•+, 34); 245 (15); 151 (47); 112 (41); 106 (19); 91 (47); 70 (100); 43 (18); 41 (15); 30 (14). | long-lasting, umami |
| 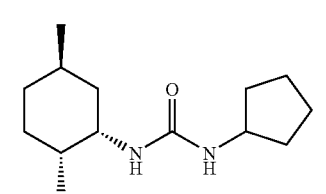 racemic | m/z (%) = 266 (M•+, 13); 223 (12); 129 (47); 112 (31); 84 (11); 70 (100); 56 (28); 55 (13); 43 (16); 41 (21). | bitter, astringent, long-lasting, salty, metallic |
| 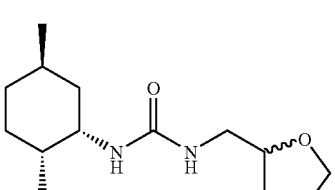 racemic | m/z (%) = 282 (M•+, 11); 239 (39); 169 (56); 112 (46); 111 (31); 102 (41); 71 (47); 70 (100); 69 (47); 30 (48). | salty, weakly umami |
| 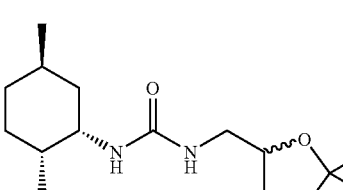 racemic | m/z (%) = 312 (M•+, 36); 297 (47); 254 (97); 211 (47); 169 (100); 117 (63); 112 (42); 73 (80); 70 (72); 30 (47). | sweet, umami |

-continued
| Structure | MS Data | Flavor Profile |
|---|---|---|
| 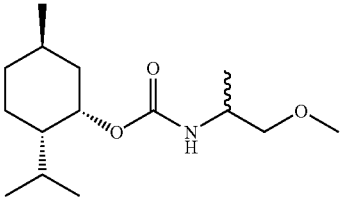 racemic | m/z (%) = 226 (37); 139 (42); 95 (35); 83 (97); 69 (44); 57 (36); 55 (42); 45 (30); 44 (100); 41 (34). | bitter, metallic, umami |
| 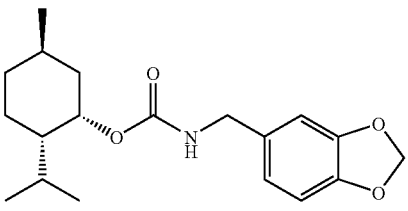 racemic | m/z (%) = 333 (M$^{\bullet+}$, 10); 196 (9); 195 (78); 194 (100); 150 (16); 135 (26); 83 (20); 69 (12); 55 (17); 41 (9). | bitter, umami |
| 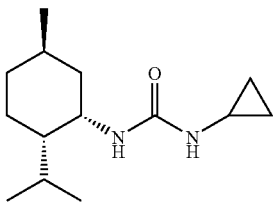 racemic | m/z (%) = 238 (M$^{\bullet+}$, 2); 83 (4); 69 (4); 58 (5); 57 (100); 56 (20); 55 (8); 43 (5); 41 (9); 32 (6). | bitter, long-lasting, salty, umami |
| 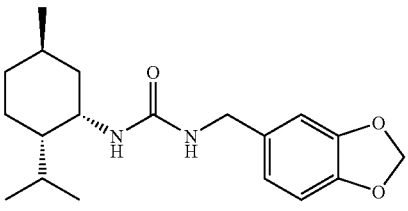 racemic | m/z (%) = 332 (M$^{\bullet+}$, 46); 194 (26); 150 (32); 134 (95); 112 (30); 70 (100); 55 (19); 43 (14); 41 (16); 30 (18). | salty, weakly umami |
| 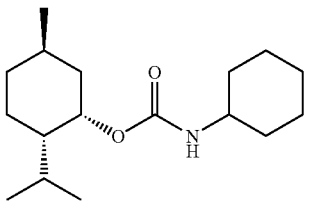 racemic | m/z (%) = 281 (M$^{\bullet+}$, 0.4); 144 (100); 138 (66); 95 (57); 83 (100); 81 (46); 69 (42); 56 (37); 55 (60); 41 (38). | weakly sweet and weakly umami |
| 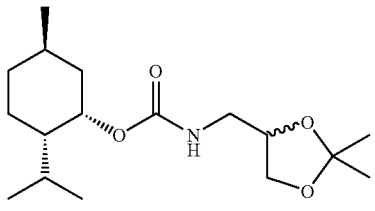 racemic | m/z (%) = 160 (24); 139 (11); 138 (18); 118 (21); 101 (100); 83 (27); 73 (15); 59 (11); 55 (15); 43 (29). | sweet, bitter, caramel, salty |

-continued
| Structure | MS Data | Flavor Profile |
|---|---|---|
| 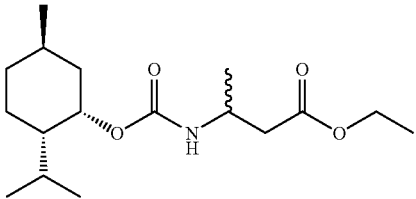 racemic | m/z (%) = 313 (M•+, 0.3); 132 (95); 130 (84); 116 (62); 95 (79); 83 (90); 81 (58); 69 (52); 55 (54); 44 (100). | bitter, dry-dusty, tingling, slightly umami |
| 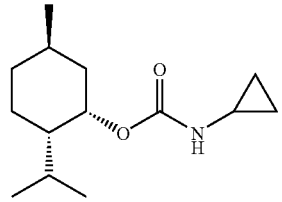 racemic | m/z (%) = 239 (M•+, 0.5); 139 (13); 97 (18); 83 (100); 81 (18); 69 (41); 57 (72); 55 (43); 43 (17); 41 (24). | bitter, salty, umami |
| 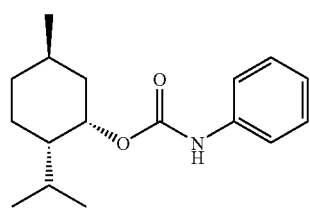 racemic | m/z (%) = 275 (M•+, 15); 138 (23); 93 (82); 83 (100); 81 (21); 69 (44); 57 (28); 55 (46); 43 (21); 41 (26). | bitter, dry, dusty, umami, dull |
| 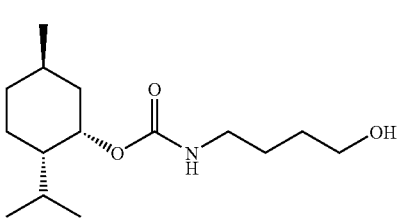 racemic | m/z (%) = 138 (49); 95 (92); 90 (38); 83 (100); 81 (57); 71 (58); 69 (50); 55 (89); 43 (48); 41 (44). | slightly bitter, salty, umami |
| 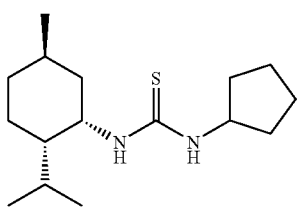 racemic | m/z (%) = 282 (M•+, 16); 145 (100); 95 (26); 83 (18); 77 (19); 69 (28); 55 (27); 43 (18); 41 (11); 28 (20). | bitter, long-lasting, umami, metallic |
| 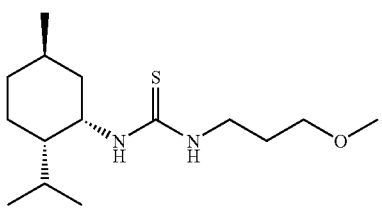 racemic | m/z (%) = 286 (M•+, 31); 149 (100); 117 (36); 112 (29); 95 (28); 90 (30); 83 (26); 55 (36); 45 (32); 41 (38). | very bitter, umami |

| Structure | MS Data | Flavor Profile |
|---|---|---|
| (racemic menthyl ethyl thiourea) | m/z (%) = 242 (M·+, 17); 193 (19); 112 (15); 105 (100); 95 (18); 69 (12); 55 (19); 44 (12); 43 (15); 41 (18). | bitter, dry-dusty, umami |
| (racemic menthyl methoxypropyl thiourea) | m/z (%) = 286 (M·+, 11); 254 (63); 149 (43); 139 (54); 90 (45); 83 (100); 69 (51); 58 (63); 55 (59); 41 (59). | bitter, slightly umami |
| (racemic menthyl cyclopropyl thiourea) | m/z (%) = 254 (M·+, 64); 117 (71); 83 (40); 69 (29); 58 (100); 57 (77); 56 (45); 55 (43); 43 (31); 41 (67). | bitter, mouthfeel, umami |

Examples

The examples serve to explain the invention, but without limiting it. Unless otherwise indicated, all data refer to weight.

Application Example 1

Spray-Dried Compositions

| | Constituent | Proportion |
|---|---|---|
| 1.1 | 4-((1S,2S,5R)-2-isopropyl-5-methyl-cyclohexyloxycarbonylamino)-butyric acid ethyl ester (11) | 3 g |
| | maltodextrin | 97 g |
| 1.2 | 1:1 mixture of 3-[3-((1S,2S,5R)-2-isopropyl-5-methyl-cyclohexyl)-ureido]-butyric acid ethyl ester (7) and 3-[3-((1R,2R,5S)-2-isopropyl-5-methyl-cyclohexyl)-ureido]-butyric acid ethyl ester (8) Synthesis Example 4 | 4 g |
| | maltodextrin | 96 g |

The constituents are dissolved in a mixture of ethanol and demineralized water and subsequently spray-dried.

Application Example 2

Aroma Composition, not According to the Invention

| Ingredient | Proportion |
|---|---|
| 10 wt. % pellitorin in 1,2-propylene glycol/diethylmalonate | 0.25 g |
| hesperetin | 2.50 g |
| phloretin | 1.50 g |
| propylene glycol | 95.75 g |

The aroma composition was used in the application the examples described below.

Application Example 3

Seasoning

| Part | Constituent | Proportion |
|---|---|---|
| A | 1:1 mixture of compounds of the formulae (7) + (8) | 0.02 g |
| | sodium chloride | 15 g |
| B | mustard seed powder | 5 g |
| | mustard aroma | 0.1 g |

Part A was weighed out. 290 ml of water were provided and added to part A while stirring and dissolved. The solution is diluted with water to 1.84 kg (pH 6.0) and subsequently freeze-dried (eutectic point: −15° C.; working vacuum: 0.52 mbar; tray temperature: −5° C. to +25° C.). The product is mixed with mustard seed powder and the mustard aroma from Part B and packaged to form a seasoning.

Application Example 4

Reaction Aroma

| Ingredient | Amount [g] |
| --- | --- |
| L-alanine | 41.0 |
| L-aspartic acid | 123.0 |
| succinic acid | 4.7 |
| Calcium chloride dihydrate | 7.0 |

-continued

| Ingredient | Amount [g] |
| --- | --- |
| L-cysteine•HCl monohydrate | 11.0 |
| dipotassium phosphate | 6.0 |
| fructose powder | 1.0 |
| l-isoleucine | 1.6 |
| potassium chloride | 228.0 |
| L-leucine | 1.6 |
| L-lysine•HCl | 3.6 |
| magnesium chloride hexahydrate | 19.0 |
| Maltodextrin | 49.0 |
| L-phenylalanine | 2.0 |
| L-proline | 74.0 |
| L-serine | 6.5 |
| L-threonine | 3.0 |
| L-valine | 9.0 |
| Water | 404.0 |

-continued

| Ingredient | Amount [g] |
| --- | --- |
| 1:1 mixture of the compounds of formulae (7) + (8), 20 wt. % in EtOH | 5.0 |

All the components were mixed at 40° C. sequentially heated to 85° C. for 10 minutes (reflex reaction). After cooling to 40° C., it was adjusted to pH 5 with potassium hydroxide. This umami reaction aroma may be incorporated instead of the pure compound ((7)+(8)) into the broth—preparations C or D of Application Example 9, 5 g of the umami reaction aroma having been used in preparation C and 13 g in preparation D.

Application Example 5

Instant Soup, Cream of Leek Type

| Constituent | A | B | C | D | E |
| --- | --- | --- | --- | --- | --- |
| potato starch | 20.0 g | 20.0 g | 20.0 g | 20.0 g | 20.0 g |
| fat powder | 25.0 g | 25.0 g | 25.0 g | 25.0 g | 25.0 g |
| Lactose | 20.0 g | 20.0 g | 20.0 g | 20.0 g | 20.0 g |
| Maltodextrin | 11.730 g | 14.729 g | 14.725 g | 14.710 g | 15.723 g |
| sodium chloride | 8.0 g | 8.0 g | 8.0 g | 8.0 g | 7.0 g |
| sodium glutamate | 3.0 g | — | — | — | — |
| spinach powder | 2.0 g | 2.0 g | 2.0 g | 2.0 g | 2.0 g |
| green leek powder | 2.0 g | 2.0 g | 2.0 g | 2.0 g | 2.0 g |
| citric acid, as powder | 0.3 g | 0.3 g | 0.3 g | 0.3 g | 0.3 g |
| hardened plant fat | 3.0 g | 3.0 g | 3.0 g | 3.0 g | 3.0 g |
| freeze-dried leek | 1.0 g | 1.0 g | 1.0 g | 1.0 g | 1.0 g |
| chicken aroma | 1.0 g | 1.0 g | 1.0 g | 1.0 g | 1.0 g |
| seasoning mixture, "green leek" type, powder | 2.0 g | 2.0 g | 2.0 g | 2.0 g | 2.0 g |
| seasoning mixture, "cooked onion" type | 0.6 g | 0.6 g | 0.6 g | 0.6 g | 0.6 g |
| yeast-seasoning mixture, "vegetable stock" type, powder | 0.3 g | 0.3 g | 0.3 g | 0.3 g | 0.3 g |
| Curcuma extract | 0.07 g | 0.07 g | 0.07 g | 0.07 g | 0.07 g |
| 1:1 mixture of compounds of the formulae (1) + (2) | — | 0.001 g | 0.005 g | 0.020 g | 0.007 g |

A = comparative preparation

B, C, D = preparations according to the invention (sodium glutamate-free)

E = preparations according to the invention (salt-reduced and sodium glutamate-free)

5 g of the respective powder mixture were blended with 100 ml of hot water each, in order to obtain a soup ready for consumption. When tasted by a panel of trained testers, Comparative Preparation A and Preparation E according to the invention were evaluated as equal in respect of their umami character and their saltiness. For Preparation B according to the invention, the umami flavor (and mouthfeel) were described as perceptible, but weaker than Preparations A and E. Preparation C according to the invention is evaluated as equal to Preparations A and E in respect of its umami character, but here an increased saltiness is also described. Preparation D according to the invention was evaluated as very pronounced in respect of umami flavor (and mouthfeel) and significantly stronger than Preparations A and E, which is further underlined by a concomitant increase in the saltiness.

Application Example 6

Instant Soup, Chicken Soup with Noodles Type

| Constituent | A | B | C | D | E |
|---|---|---|---|---|---|
| Starch | 16.0 g | 16.0 g | 16.0 g | 16.0 g | 16.0 g |
| sodium chloride | 7 g | 7 g | 7 g | 7 g | 5 g |
| saccharose, refined | 3.2 g | 3.2 g | 3.2 g | 3.2 g | 3.2 g |
| sodium glutamate | 3.2 g | — | — | — | — |
| sodium inosinate/sodium guanylate in the ratio 1:1 | 0.8 g | 0.8 g | 0.8 g | 0.8 g | 0.8 g |
| acid-hydrolysed plant protein | 8.0 g | 8.0 g | 8.0 g | 8.0 g | 8.0 g |
| fat powder | 2.0 g | 2.0 g | 2.0 g | 2.0 g | 2.0 g |
| vegetable fat, spray-dried | 1.0 g | 1.0 g | 1.0 g | 1.0 g | 1.0 g |
| freeze-dried chicken meat, in pieces | 2.0 g | 2.0 g | 2.0 g | 2.0 g | 2.0 g |
| soup noodles | 32.0 g | 32.0 g | 32.0 g | 32.0 g | 32.0 g |
| Maltodextrin | 12.160 g | 15.359 g | 14.155 g | 14.140 g | 15.152 g |
| Chinese vegetables, freeze-dried | 4.6 g | 4.6 g | 4.6 g | 4.6 g | 4.6 g |
| chicken aroma | 8.0 g | 8.0 g | 8.0 g | 8.0 g | 8.0 g |
| food coloring riboflavin | 0.04 g | 0.04 g | 0.04 g | 0.04 g | 0.04 g |
| 1:1 mixture of compounds of the formulae (7) + (8) | — | 0.001 g | 0.005 g | 0.02 g | 0.008 g |
| aroma composition according to Application Example 2.1 | — | — | 1.2 g | 1.2 g | 1.2 g |

A = comparative preparation
B, C, D = preparations according to the invention (sodium glutamate-free)
E = preparations according to the invention (salt-reduced and sodium glutamate-free)

4.6 g of the respective powder mixture were cooked for 10 minutes in 100 ml of water each, in order to obtain a soup ready for consumption. When tasted by a panel of trained testers, Comparative Preparation A and Preparation E according to the invention were evaluated as equal in respect of their umami character and their saltiness. For Preparation B according to the invention, the umami flavor (and mouthfeel) were described as perceptible, but weaker than Preparations A and E. Preparation C according to the invention is evaluated as equal to Preparations A and E in respect of its umami character, but here an increased saltiness is also described. Preparation D according to the invention was evaluated as very pronounced in respect of umami flavor (and mouthfeel) and significantly stronger than Preparations A and E, which is further underlined by a concomitant increase in the saltiness.

Application Example 7

Seasoning Mixture, "Pepper" Type

| Constituent | A | B | C | D | E |
|---|---|---|---|---|---|
| milk protein | 0.8 g | 0.8 g | 0.8 g | 0.8 g | 0.8 g |
| carob bean powder | 2.0 g | 2.0 g | 2.0 g | 2.0 g | 2.0 g |
| corn starch | 22.0 g | 27.998 g | 27.985 g | 27.940 g | 29.970 g |
| sodium chloride | 14.0 g | 14.0 g | 14.0 g | 14.0 g | 12.0 g |
| paprika powder | 13.0 g | 13.0 g | 13.0 g | 13.0 g | 13.0 g |
| tomato powder | 13.0 g | 13.0 g | 13.0 g | 13.0 g | 13.0 g |
| Saccharose | 4.0 g | 4.0 g | 4.0 g | 4.0 g | 4.0 g |
| garlic powder | 0.5 g | 0.5 g | 0.5 g | 0.5 g | 0.5 g |
| hardened plant fat | 8.0 g | 8.0 g | 8.0 g | 8.0 g | 8.0 g |
| fat powder | 11.0 g | 11.0 g | 11.0 g | 11.0 g | 11.0 g |
| sodium glutamate | 6.0 g | — | — | — | — |
| food coloring beetroot and paprika | 2.0 g | 2.0 g | 2.0 g | 2.0 g | 2.0 g |
| aroma "pepper" type | 2.0 g | 2.0 g | 2.0 g | 2.0 g | 2.0 g |
| aroma "pizza" type | 1.2 g | 1.2 g | 1.2 g | 1.2 g | 1.2 g |
| aroma "tomato" type | 0.4 g | 0.4 g | 0.4 g | 0.4 g | 0.4 g |
| black pepper extract | 0.1 g | 0.1 g | 0.1 g | 0.1 g | 0.1 g |
| compound of the formula (1) | — | 0.002 g | 0.015 g | 0.060 g | 0.03 g |

A = comparative preparation
B, C, D = preparations according to the invention (sodium glutamate-free)
E = preparations according to the invention (salt-reduced and sodium glutamate-free)

100 g of neck pork chop were respectively sprinkled uniformly with 1.7 g of Preparations A, B, C and D and roasted. When tasted by a panel of trained testers, Comparative Preparation A and Preparation E according to the invention were evaluated as equal in respect of their umami character and their saltiness. For Preparation B according to the invention, the umami flavor (and mouthfeel) were described as perceptible, but weaker than Preparations A and E. Preparation C according to the invention is evaluated as equal to Preparations A and E in respect of its umami character, but here an increased saltiness is also described. Preparation D according to the invention was evaluated as very pronounced in respect of umami flavor (and mouthfeel) and significantly stronger than Preparations A and E, which is further underlined by a concomitant increase in the saltiness.

Application Example 8

Tomato Ketchup

| Constituent | A | B | C | D |
|---|---|---|---|---|
| sodium glutamate | 0.40 g | — | — | — |
| sodium chloride | 2 g | 1 g | 2 g | 1 g |
| starch, Farinex WM 55 | 1 g | 1 g | 1 g | 1 g |
| Sucrose | 12 g | 9.2 g | 9.2 g | 9.2 g |
| tomato concentrate 2 times | 40 g | 40 g | 40 g | 40 g |
| glucose syrup 80 Brix | 18 g | 18 g | 18 g | 18 g |
| brandy vinegar 10% | 7 g | 7 g | 7 g | 7 g |
| Water | 19.60 g | 23.80 g | 22.30 g | 23.25 g |
| aroma composition according to Application Example 2.1 | — | — | 0.4 g | 0.4 g |
| 1% strength solution of a 1:1 mixture of compounds of the formulae (11) + (12) in propylene glycol | — | — | 0.10 g | 0.15 g |

A = comparative preparation
B = comparative preparation (salt- and sugar-reduced, sodium glutamate-free)
C = preparations according to the invention (sodium glutamate-free, sugar-reduced)
D = preparations according to the invention (salt- and sugar-reduced, sodium glutamate-free)

The ingredients are mixed in the order indicated and the finished ketchup is homogenized with the aid of a stirrer, put into bottles and sterilized.

Application Example 9

Broth

| Constituent | A | B | C | D | E |
|---|---|---|---|---|---|
| fat powder | 8.77 g | 8.77 g | 8.77 g | 8.77 g | 8.77 g |
| sodium glutamate | 8.77 g | 5 g | 5 g | — | — |
| yeast extract powder | 12.28 g | 12.28 g | 12.28 g | 12.28 g | 12.28 g |
| sodium chloride | 29.83 g | 29.83 g | 29.83 g | 29.83 g | 26.83 g |
| Maltodextrin | 37.28 g | 41.050 g | 41.047 g | 46.020 g | 49.020 g |
| natural vegetable extract | 3.07 g | 3.07 g | 3.07 g | 3.07 g | 3.07 g |
| 1:1 mixture of compounds of the formulae (7) + (8) | — | — | 0.003 g | 0.030 g | 0.030 g |

A = comparative preparation
B = comparative preparation (sodium glutamate-reduced)
C = preparations according to the invention
D = preparations according to the invention (sodium glutamate-free)
E = preparations according to the invention (salt-reduced and sodium glutamate-free)

15 g of the respective powder mixture were blended with 1000 ml of hot water each. When tasted by a panel of trained testers, Preparations C and D according to the invention were evaluated as very pronounced in respect of their umami flavor (and mouthfeel) and significantly stronger than sodium glutamate-reduced Comparative Preparation B. For both of them, an enhanced saltiness was found in comparison with Preparation A. Sodium glutamate-free, salt-reduced Preparation E was reported as very similar to Comparative Preparation A in respect of its umami flavor (and mouthfeel) and its saltiness.

Application Example 10

Seasoning Mixture for Potato Chips

| Constituent | A | B | C | D | E |
|---|---|---|---|---|---|
| sodium glutamate | 3.50 g | 2.00 g | 2.00 g | — | 1.00 g |

-continued

| Constituent | A | B | C | D | E |
|---|---|---|---|---|---|
| cheese powder | 10.00 g | 10.00 g | 10.00 g | 10.00 g | 10.00 g |
| garlic powder | 2.00 g | 2.00 g | 2.00 g | 2.00 g | 2.00 g |

-continued

| Constituent | A | B | C | D | E |
|---|---|---|---|---|---|
| whey powder | 38.86 g | 40.36 g | 40.06 g | 41.91 g | 44.76 g |
| seasoning extract oil | 0.20 g | 0.20 g | 0.20 g | 0.20 g | 0.20 g |
| paprika powder | 9.80 g | 9.80 g | 9.80 g | 9.80 g | 9.80 g |
| sodium chloride | 21.00 g | 21.00 g | 21.00 g | 21.00 g | 17.00 g |
| tomato powder | 9.00 g | 9.00 g | 9.00 g | 9.00 g | 9.00 g |
| dry aroma | 2.50 g | 2.50 g | 2.50 g | 2.50 g | 2.50 g |
| silicon dioxide | 0.02 g | 0.02 g | 0.02 g | 0.02 g | 0.02 g |
| Plant oil | 0.02 g | 0.02 g | 0.02 g | 0.02 g | 0.02 g |
| onion powder | 3.00 g | 3.00 g | 3.00 g | 3.00 g | 3.00 g |
| cream aroma concentrate | 0.03 g | 0.03 g | 0.03 g | 0.03 g | 0.03 g |
| cheese aroma | 0.03 g | 0.03 g | 0.03 g | 0.03 g | 0.03 g |
| tomato aroma concentrate | 0.04 g | 0.04 g | 0.04 g | 0.04 g | 0.04 g |
| Spray-dried composition according to Example 1.1 | — | — | 0.30 g | 0.45 g | 0.60 g |

A = comparative preparation
B = comparative preparation (sodium glutamate-reduced)
C = preparations according to the invention (sodium glutamate-reduced)
D = preparations according to the invention (sodium glutamate-free)
E = preparations according to the invention (sodium glutamate-and salt-reduced)

6 g of the seasoning mixture were applied to 94 g of potato chips. When tasted by a panel of trained testers, Preparations C and D according to the invention were evaluated as very pronounced in respect of their umami flavor (and mouthfeel) and significantly stronger than sodium glutamate-reduced Comparative Preparation B. For both of them, an enhanced saltiness was found in comparison with Preparation A. Sodium glutamate-reduced, salt-reduced Preparation E was reported as rounded in respect of its umami flavor (and mouthfeel) and its saltiness, and more intense than Comparative Preparation A.

Application Example 11

White Sauce

| Constituent | A | B | C | D | E |
|---|---|---|---|---|---|
| maltodextrin | 25.98 g | 27.18 g | 27.08 g | 27.58 g | 28.43 g |
| sodium chloride | 7.50 g | 7.50 g | 7.50 g | 7.50 g | 6.00 g |
| sodium glutamate | 2.00 g | 0.80 g | 0.80 g | — | 0.80 g |
| plant fat | 5.00 g | 5.00 g | 5.00 g | 5.00 g | 5.00 g |
| pepper, white | 0.02 g | 0.02 g | 0.02 g | 0.02 g | 0.02 g |
| onion powder | 1.50 g | 1.50 g | 1.50 g | 1.50 g | 1.50 g |
| Pre-agglomerated corn starch | 30.00 g | 30.00 g | 30.00 g | 30.00 g | 30.00 g |
| fat powder | 28.00 g | 28.00 g | 28.00 g | 28.00 g | 28.00 g |
| Spray-dried composition according to Example 1.2 | — | — | 0.10 g | 0.40 g | 0.25 g |

A = comparative preparation
B = comparative preparation (sodium glutamate-reduced)
C = preparations according to the invention (sodium glutamate-reduced)
D = preparations according to the invention (sodium glutamate-free)
E = preparations according to the invention (sodium glutamate- and salt-reduced)

90 g of the sauce mixture were blended with 1000 ml hot water and stirred vigorously with a whisk. When tasted by a panel of trained testers, Preparations C and D according to the invention were evaluated as very pronounced in respect of their umami flavor (and mouthfeel) and significantly stronger than sodium glutamate-reduced Comparative Preparation B. For both of them, an enhanced saltiness was found in comparison with Preparation A. Sodium glutamate-reduced, salt-reduced Preparation E was reported as significantly rounded in respect of its umami flavor (and mouthfeel) and its saltiness, and more intense than Comparative Preparation A.

Application Example 12

Brown Sauce

| Constituent | A | B | C | D | E |
|---|---|---|---|---|---|
| starch | 40.00 g | 40.00 g | 40.00 g | 40.00 g | 40.00 g |
| maltodextrin | 33.10 g | 33.80 g | 33.66 g | 34.70 g | 35.07 g |
| sodium chloride | 6.00 g | 6.00 g | 6.00 g | 6.00 g | 4.50 g |
| caramel, spray-dried | 5.00 g | 5.00 g | 5.00 g | 5.00 g | 5.00 g |
| yeast extract powder | 3.00 g | 3.00 g | 3.00 g | 3.00 g | 3.00 g |
| sodium glutamate | 2.00 g | 1.30 g | 1.30 g | — | 1.30 g |
| sugar | 0.50 g | 0.50 g | 0.50 g | 0.50 g | 0.50 g |
| fat powder | 5.00 g | 5.00 g | 5.00 g | 5.00 g | 5.00 g |
| tomato powder | 3.00 g | 3.00 g | 3.00 g | 3.00 g | 3.00 g |
| natural vegetable extract | 1.00 g | 1.00 g | 1.00 g | 1.00 g | 1.00 g |
| onion extract | 0.30 g | 0.30 g | 0.30 g | 0.30 g | 0.30 g |
| pepper extract | 0.10 g | 0.10 g | 0.10 g | 0.10 g | 0.10 g |
| dry aroma | 1.00 g | 1.00 g | 1.00 g | 1.00 g | 1.00 g |
| Spray-dried composition according to Example 1.2 | — | — | 0.70 g | 2.00 g | 0.70 g |

A = comparative preparation
B = comparative preparation (sodium glutamate-reduced)
C = preparations according to the invention (sodium glutamate-reduced)
D = preparations according to the invention (sodium glutamate-free)
E = preparations according to the invention (sodium glutamate-and salt-reduced)

90 g of the sauce mixture were blended with 1000 ml hot water and stirred vigorously with a whisk. When tasted by a panel of trained testers, Preparations C and D according to the invention were evaluated as very pronounced in respect of their umami flavor (and mouthfeel) and significantly stronger than sodium glutamate-reduced Comparative Preparation B. For both of them, an enhanced saltiness was found in comparison with Preparation A. Sodium glutamate-reduced, salt-reduced Preparation E was reported as significantly rounded in respect of its umami flavor (and mouthfeel) and its saltiness, and more intense than Comparative Preparation A.

Application Example 13

Tomato Soup

| Constituent | A | B | C | D | E |
|---|---|---|---|---|---|
| water | 50.65 g | 50.80 g | 50.799 g | 51.035 g | 51.29 g |
| plant oil | 5.50 g | 5.50 g | 5.50 g | 5.50 g | 5.50 g |
| tomato paste | 24.00 g | 24.00 g | 24.00 g | 24.00 g | 24.00 g |
| cream | 1.05 g | 1.05 g | 1.05 g | 1.05 g | 1.05 g |
| sugar | 2.00 g | 2.00 g | 2.00 g | 2.00 g | 2.00 g |
| sodium chloride | 1.70 g | 1.70 g | 1.70 g | 1.70 g | 1.20 g |
| sodium glutamate | 0.40 g | 0.25 g | 0.25 g | — | 0.25 g |
| wheat flour | 5.50 g | 5.50 g | 5.50 g | 5.50 g | 5.50 g |
| starch | 1.20 g | 1.20 g | 1.20 g | 1.20 g | 1.20 g |
| cubed tomatoes | 8.00 g | 8.00 g | 8.00 g | 8.00 g | 8.00 g |
| Spray-dried composition according to Example 1.2 | — | — | 0.001 g | 0.015 g | 0.010 g |

A = comparative preparation
B = comparative preparation (sodium glutamate-reduced)
C = preparations according to the invention (sodium glutamate-reduced)
D = preparations according to the invention (sodium glutamate-free)
E = preparations according to the invention (sodium glutamate-and salt-reduced)

The solid constituents were weighed out, mixed, and added to the water. The plant oil was dosed in and the tomato paste was added. The mixture was cooked while stirring. When tasted by a panel of trained testers, Comparative Preparation A and Preparation E according to the invention were evaluated as equal in respect of their umami character and their saltiness. For Preparation B according to the invention, the umami flavor (and mouthfeel) were described as perceptible, but weaker than Preparations A and E. Preparation C according to the invention is evaluated as equal to Preparations A and E in respect of its umami character, but here an increased saltiness is also described. Preparation D according to the invention was evaluated as very pronounced in respect of umami flavor (and mouthfeel) and significantly stronger than Preparations A and E, which is further underlined by a concomitant increase in the saltiness.

Application Example 14

Application in a Sugar-Free Chewing Gum

| Part | Ingredient | Amount in wt. % |
|---|---|---|
| A | chewing gum base, Company "Jagum T" | 29.995 |
| B | sorbite, powdered | 39.00 |
| | Isomalt ® (Palatinit GmbH) | 9.50 |
| | Xylite | 2.00 |
| | Mannite | 3.00 |
| | Aspartam ® | 0.10 |
| | Acesulfam ® K | 0.10 |
| | Emulgum ® (Colloides Naturels, Inc.) | 0.30 |
| C | Sorbitol, 70% | 14.00 |
| | Glycerine | 1.00 |
| D | aroma composition corresponding to Application Example 2.1 | 1.00 |
| | 1:1 mixture of the compounds (11) + (12) | 0.005 |

Parts A to D were mixed and kneaded intensively. The raw compound may then for example be processed in the form of thin strips to form chewing gum ready for consumption.

Application Example 15

Application in a Green Tea Beverage

| Ingredient | Amount in wt. % |
|---|---|
| green tea concentrate | 18.00 |
| 1% strength solution of an equimolar mixture of compounds of the formulae (7) and (8) in propylene glycol | 0.002 |
| demineralized water | 81.998 |

The green tea concentrate is mixed with the 1% strength solution of an equimolar mixture of formulae (7) and (8) in propylene glycol. It is then filled up with the demineralized water and thoroughly mixed again. The product is then filtered, packaged ready for use and sterilized at 118° C. The flavor is evaluated by a panel of trained testers as significantly preferably compared with the non-aromatized green tea concentrate.

Application Example 16

Beef Seasoning Mixture for (Ready) Noodles

| Ingredient | wt. % |
|---|---|
| beef fat aroma | 5 |
| Caramel | 3.00 |
| citric acid (anhydrous) | 0.40 |
| chives (dried) | 2.00 |
| maltodextrin (from tapioca) | 10.30 |
| monosodium glutamate | 15.00 |
| onion powder | 5.00 |
| Ribotide | 0.80 |
| sodium chloride | 45.65 |
| Sugar | 2.80 |
| sweet whey powder | 6.50 |
| 1% strength solution of an equimolar mixture of compounds of the formulae compounds of the formulae (7) + (8) in propylene glycol | 0.05 |

All the ingredients are mixed until a homogeneous mixture is obtained.

Application Example 17

(Ready) Noodles

| Part | Ingredient | wt. % |
|---|---|---|
| A | wheat flour | 62.00 |
|   | potato starch | 10.90 |
| B | Salt | 1.10 |
|   | guar seed flour | 0.06 |
|   | sodium carbonate | 0.07 |
|   | potassium carbonate | 0.25 |
|   | $Na_2H_2P_2O_7$ | 0.07 |
|   | 1% strength solution of an equimolar mixture of compounds of the formulae compounds of the formulae (11) + (12) in propylene glycol | 0.05 |
| C | Water | 25.45 |

A suspension of the ingredients B in water is added to a mixture of the ingredients A and kneaded to form die. After the girl has rested for about 5 minutes, it is processed with the aid of a noodle machine into sheets which are trimmed into a conventional shape in a final working step. The noodles are ready for consumption after a cooking time of 3 minutes and enriched with 8 g of the beef seasoning mixture (Application Example 16).

The flavor of a 0.5% American beef extract as the base (solid dark line) was compared with the aid of tasting by a panel of trained testers with the flavor firstly of such a base to which 1 ppm of a mixture of 1-((1S,2S,5R)-2-isopropyl-5-methyl-cyclohexyl)-3-(3-methoxy-propyl)-urea (1) and 1-((1R,2R,5S)-2-Isopropyl-5-methyl-cyclohexyl)-3-(3-methoxy-propyl)-urea (2) was added (solid light line), and secondly such a base to which 0.05 wt. % MSG was added (dotted line).

The testers evaluated the strength of the test directions indicated, in each case by specifying marks on a scale of from 0 (no corresponding flavor) to 8 (very strong corresponding flavor). The average values of the respective marks are represented.

Figure 1:
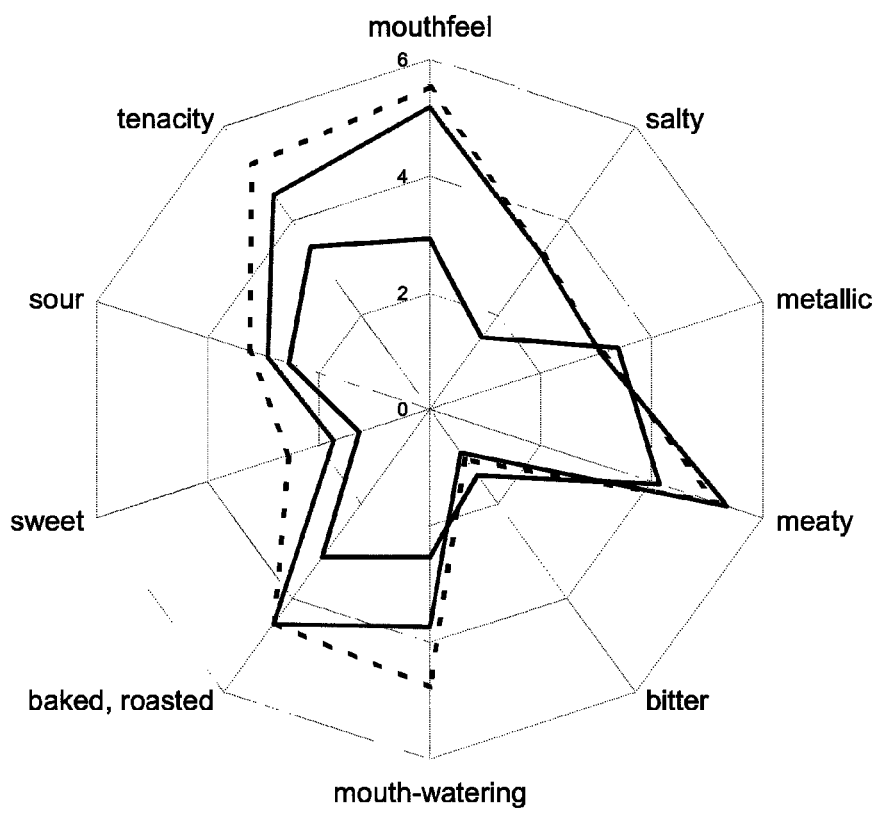
FIG. 1: Flavor comparison of a mixture of 1-((1S,2S,5R)-2-isopropyl-5-methyl-cyclohexyl)-3-(3-methoxy-propyl)-urea (1) and 1-((1R,2R,5S)-2-isopropyl-5-methyl-cyclohexyl)-3-(3-methoxy-propyl)-urea (2) with sodium glutamate.
Figure 2:
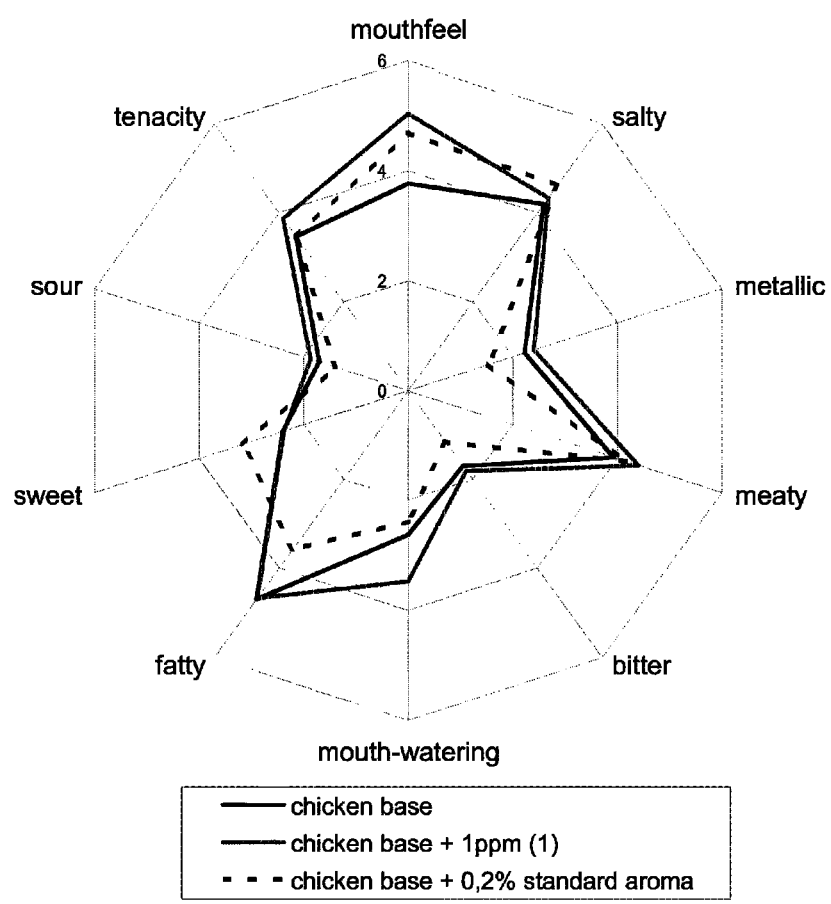

FIG. 2: Flavor comparison of 1-((1S,2S,5R)-2-isopropyl-5-methyl-cyclohexyl)-3-(3-methoxy-propyl)-urea (1) with a standard chicken aroma containing sodium glutamate.

The flavor of the chicken base (solid dark line) was compared with the aid of tasting by a panel of trained testers with the flavor firstly of such a base to which 1 ppm of 1-((1S,2S,5R)-2-Isopropyl-5-methyl-cyclohexyl)-3-(3-methoxy-propyl)-urea (1) was added (solid light line), and secondly such a base to which 0.2 wt. % of a standard chicken aroma containing sodium glutamate was added (dotted line).

The testers evaluated the strength of the test directions indicated, in each case by specifying marks on a scale of from 0 (no corresponding flavor) to 8 (very strong corresponding flavor). The average values of the respective marks are represented.

Figure 3:

FIG. 3: Flavor comparison of a 1:1 mixture of 3-[3-((1S,2S,5R)-2-isopropyl-5-methyl-cyclohexyl)-ureido]-butyric acid ethyl ester (7) and 3-[3-((1R,2R,5S)-2-isopropyl-5-methyl-cyclohexyl)-ureido]-butyric acid ethyl ester (8) with sodium glutamate.

The flavor of a 0.5% American beef extract as the base (solid dark line) was compared with the aid of tasting by a panel of trained testers with the flavor firstly of such a base to which 5 ppm of a mixture of 3-[3-((1S,2S,5R)-2-Isopropyl-5-methyl-cyclohexyl)-ureido]-butyric acid ethyl ester (7) and 3-[3-((1R,2R,5S)-2-Isopropyl-5-methyl-cyclohexyl)-ureido]-butyric acid ethyl ester (8) were added (solid light line), and secondly such a base to which 0.05 wt. % MSG was added (dotted line).

The testers evaluated the strength of the test directions indicated, in each case by specifying marks on a scale of from 0 (no corresponding flavor) to 8 (very strong corresponding flavor). The average values of the respective marks are represented.

SPECIFIC EMBODIMENTS

Specific embodiment one comprises a use of a compound or a mixture consisting of two or more compounds or containing one or more compounds selected from the group consisting of compounds of the formulae (I) and (ent-I)

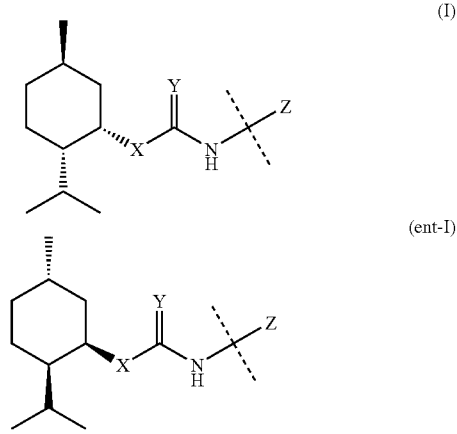

wherein the dashed line respectively marks the bond which links the organic residue Z to the neighboring nitrogen atom in formula (I) or (ent-I), and wherein the following apply independently of one another in the formulae (I) and (ent-I):

X=NH or O;

Y=O, S or NR1, where R1 denotes hydrogen, methyl, ethyl, propyl or isopropyl; and Z=organic residue having at most 15 C atoms, as a flavor material or flavor material mixture.

Specific embodiment two comprises the use of compound or a mixture as defined in the specific embodiment one, wherein (i) the compound of formula (I) or (ent-I) or (ii) one, two, more than two or all compounds of the formulae (I) and (ent-I) in the mixture are selected from the group consisting of:

(1) 1-((1S,2S,5R)-2-isopropyl-5-methyl-cyclohexyl)-3-(3-methoxy-propyl)-urea, (2) 1-((1R,2R,5S)-2-isopropyl-5-methyl-cyclohexyl)-3-(3-methoxy-propyl)-urea, (3) 1-(3-hydroxy-propyl)-3-((1S,2S,5R)-2-isopropyl-5-methyl-cyclohexyl)-urea, (4) 1-(3-hydroxy-propyl)-3-((1R,2R,5S)-2-isopropyl-5-methyl-cyclohexyl)-urea, (5) 1-((1S,2S,5R)-2-isopropyl-5-methyl-cyclohexyl)-3-(2-methoxy-1-methyl-ethyl)-urea, (6) 1-((1R,2R,5S)-2-isopropyl-5-methyl-cyclohexyl)-3-(2-methoxy-1-methyl-ethyl)-urea, (7) 3-[3-((1S,2S,5R)-2-isopropyl-5-methyl-cyclohexyl)-ureido]-butyric acid ethyl ester, (8) 3-[3-((1R,2R,5S)-2-isopropyl-5-methyl-cyclohexyl)-ureido]-butyric acid ethyl ester, (9) (3-methoxy-propyl)-carbamic acid (1S,2S,5R)-2-isopropyl-5-methyl-cyclohexyl ester,

(10) (3-methoxy-propyl)-carbamic acid (1R,2R,5S)-2-isopropyl-5-methyl-cyclohexyl ester,

(11) 4-((1S,2S,5R)-2-isopropyl-5-methyl-cyclohexyloxycarbonylamino)-butyric acid ethyl ester and

(12) 4-((1R,2R,5S)-2-isopropyl-5-methyl-cyclohexyloxycarbonylamino)-butyric acid ethyl ester.

Specific embodiment three comprises the use of a mixture as defined in one of the preceding specific embodiments, wherein the mixture contains one or more pairs of compounds of formulae (I) and (ent-I) or consists of one or more such pairs, each pair consisting of a compound of the formula (I) and a compound of the formula (ent-I) as defined in one of the preceding specific embodiments, wherein the meanings of X and Y in the compound of formula (I) are respectively identical to the meanings of X and Y in the compound of formula (ent-I) and wherein (a) the meaning of Z in the compound of formula (I) is identical to the meaning of Z in the compound of formula (ent-I) or (b) Z in the compound of formula (I) and Z in the compound of formula (ent-I) contain or one or more chiral centers and differ only by the absolute configuration at one, several or all of these chiral centers, wherein each pair is preferably an enantiomer or epimer pair.

Specific embodiment four comprises a use of a mixture as a flavor material mixture, which consists of the following components or contains them:

(a) a compound selected from the group consisting of compounds of the formulae (I) and (ent-I) as defined in one of the preceding specific embodiments or a mixture consisting of two or more compounds or containing one or more compounds selected from the group consisting of compounds of the formulae (I) and (ent-I) as defined in one of the preceding specific embodiments;

and (b) a compound selected from the group consisting of compounds of the formulae (II), (ent-II), (III), (ent-III), (IV), (ent-IV) or a mixture consisting of two or more compounds or containing one or more compounds selected from the group consisting of compounds of the formulae (II), (ent-II), (III), (ent-III), (IV), (ent-IV):

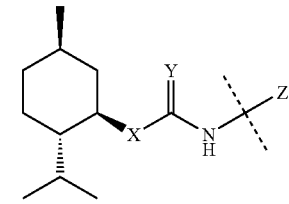

(II)

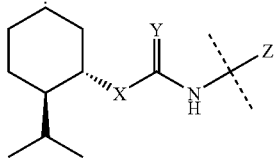

(ent-II)

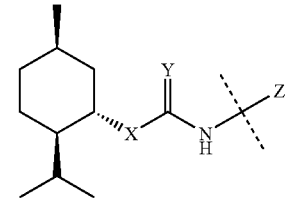

(III)

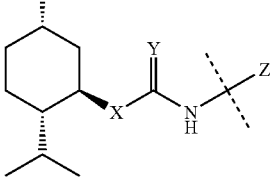

(ent-III)

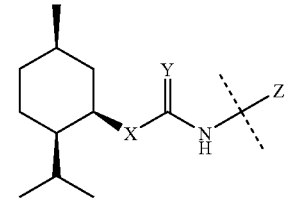

(IV)

(ent-IV)

wherein X, Y and Z in the formulae (II), (ent-II), (III), (ent-III), (IV), (ent-IV) respectively have, independently of one another, one of the meanings specified in one of the preceding specific embodiments for the formulae (I) and (ent-I), and wherein the weight ratio of (a) the total amount of compounds of formulae (I) and (ent-I) to (b) the total amount of compounds of formulae (II), (ent-II), (III), (ent-III), (IV) and (ent-IV) in the flavor material mixture is at least 60:40, preferably at least 90:10, particularly preferably at least 95:5.

Specific embodiment five comprises the use of a compound as defined in specific embodiment one or two or a mixture as defined in one of the preceding specific embodiments for producing, imparting, modifying and/or enhancing an umami flavor and/or saltiness.

Specific embodiment six comprises a single compound or mixture consisting of two or more compounds or containing one or more compounds selected from the group consisting of compounds of the formulae (I) and (ent-I)

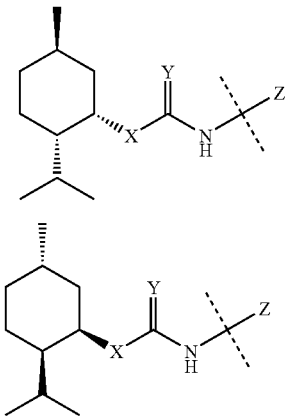

wherein the dashed line respectively marks the bond which links the organic residue Z to the neighboring nitrogen atom in formula (I) or (ent-I), and wherein the following apply independently of one another in the formulae (I) and (ent-I):

X=NH or O;

Y=O, S or NR1, where R1 denotes hydrogen, methyl, ethyl, propyl or isopropyl; and Z=organic residue consisting of carbon and hydrogen atoms and optionally oxygen atoms, wherein the sum of the number of carbon and oxygen atoms is at most 15 and the number of oxygen atoms is at most 4, and the atom by which the organic residue Z is bound to the neighboring nitrogen in formula (I) or (ent-I) is carbon, with the condition that the organic residue Z does not contain a C—C double or triple bond, contains at most one aromatic ring, and is not a group —C(=$Y^2$)—R2 in which $Y^2$ has any of the meanings specified above for Y and R2 is any organic residue, Z is not —C(R5)(R6)-C(=O)OR4, where R4 denotes H, methyl, ethyl, propyl, iso-propyl, butyl, iso-butyl or tert.-butyl and R5 and R6 independently of one another denote H or an organic residue, if X=NH and Y=O, then Z is not neomenthyl, 2-methyl-cyclohexyl or phenyl, and if X=NH and Y=S, then Z is not neomenthyl or phenyl, and if X=O and Y=O, then Z does not denote ethyl, hydroxy-ethyl, 1-phenylethyl, 2-phenylethyl, 2-hydroxy-1-methyl-2-phenylethyl, isopropyl, 2-hydroxy-1-methyl-ethyl, cyclohexyl, 4-hydroxyphenyl, 2-hydroxy-5-methylphenyl or 2,4,7-trioxa-3,3,8-trimethylbicyclo[3.3.0]octan-6-ylmethyl.

Specific embodiment seven comprises the single compound or mixture as defined in specific embodiment six, wherein (i) the compound of formula (I) or (ent-I) or (ii) one, two, more than two or all compounds of the formulae (I) and (ent-I) in the mixture are selected from the group consisting of:

(1) 1-((1S,2S,5R)-2-isopropyl-5-methyl-cyclohexyl)-3-(3-methoxy-propyl)-urea, (2) 1-((1R,2R,5S)-2-isopropyl-5-methyl-cyclohexyl)-3-(3-methoxy-propyl)-urea, (3) 1-(3-hydroxy-propyl)-3-((1S,2S,5R)-2-isopropyl-5-methyl-cyclohexyl)-urea, (4) 1-(3-hydroxy-propyl)-3-((1R,2R,5S)-2-isopropyl-5-methyl-cyclohexyl)-urea, (5) 1-((1S,2S,5R)-2-isopropyl-5-methyl-cyclohexyl)-3-(2-methoxy-1-methyl-ethyl)-urea, (6) 1-((1R,2R,5S)-2-isopropyl-5-methyl-cyclohexyl)-3-(2-methoxy-1-methyl-ethyl)-urea, (7) 3-[3-((1S,2S,5R)-2-isopropyl-5-methyl-cyclohexyl)-ureido]-butyric acid ethyl ester, (8) 3-[3-((1R,2R,5S)-2-isopropyl-5-methyl-cyclohexyl)-ureido]-butyric acid ethyl ester, (9) (3-Methoxy-propyl)-carbamic acid (1S,2S,5R)-2-isopropyl-5-methyl-cyclohexyl ester,

(10) (3-methoxy-propyl)-carbamic acid (1R,2R,5S)-2-isopropyl-5-methyl-cyclohexyl ester,

(11) 4-((1S,2S,5R)-2-isopropyl-5-methyl-cyclohexyloxycarbonylamino)-butyric acid ethyl ester and

(12) 4-((1R,2R,5S)-2-isopropyl-5-methyl-cyclohexyloxycarbonylamino)-butyric acid ethyl ester.

Specific embodiment eight comprises the mixture as defined in either of specific embodiments six and seven, wherein the mixture contains one or more pairs of compounds of formulae (I) and (ent-I) or consists of one or more such pairs, each pair consisting of a compound of the formula (I) and a compound of the formula (ent-I) as defined in one of the preceding specific embodiments, wherein the meanings of X and Y in the compound of formula (I) are respectively identical to the meanings of X and Y in the compound of formula (ent-I), and wherein (a) the meaning of Z in the compound of formula (I) is identical to the meaning of Z in the compound of formula (ent-I) or (b) Z in the compound of formula (I) and Z in the compound of formula (ent-I) contain or one or more chiral centers and differ only by the absolute configuration at one, several or all of these chiral centers Z, wherein each pair is preferably an enantiomer or epimer pair.

Specific embodiment nine comprises a mixture, which consists of the following components or contains them:

(a) a compound selected from the group consisting of compounds of the formulae (I) and (ent-I) as defined in either of specific embodiments six or seven or a mixture consisting of two or more compounds or containing one or more compounds selected from the group consisting of compounds of the formulae (I) and (ent-I) as defined in either of specific embodiment six or seven or containing a mixture as defined in specific embodiment eight;

and (b) a compound selected from the group consisting of compounds of the formulae (II), (ent-II), (III), (ent-III), (IV), (ent-IV) or a mixture consisting of two or more compounds or containing one or more compounds selected from the group consisting of compounds of the formulae (II), (ent-II), (III), (ent-III), (IV), (ent-IV):

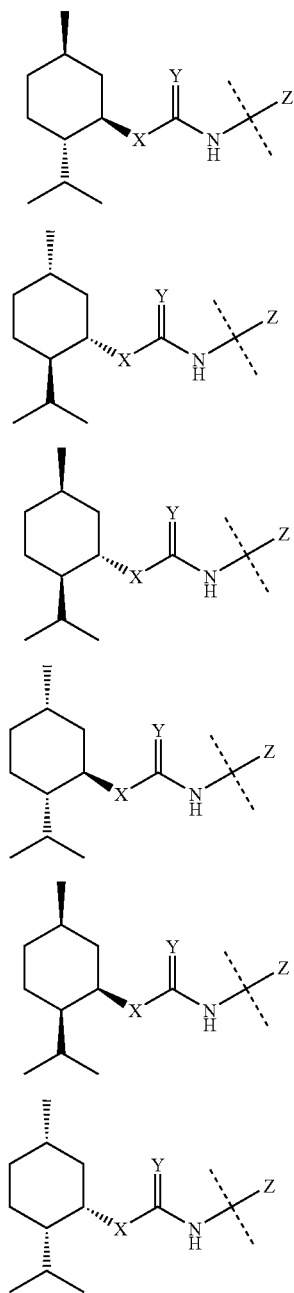

wherein X, Y and Z in the formulae (II), (ent-II), (III), (ent-III), (IV), (ent-IV) respectively have, independently of one another, one of the meanings specified in one of the preceding specific embodiments for the formulae (I) and (ent-I), and wherein the weight ratio of (a) the total amount of compounds of formulae (I) and (ent-I) to (b) the total amount of compounds of formulae (II), (ent-II), (III), (ent-III), (IV) and (ent-IV) in the flavor material mixture is at least 60:40, preferably at least 90:10, particularly preferably at least 95:5.

Specific embodiment ten comprises a composition, in particular composition suitable for consumption, comprising or consisting of an effective flavoring amount of a compound or a mixture as defined in one of the preceding specific embodiments and one or more further constituents suitable for consumption.

Specific embodiment eleven comprises the use of compounds as defined in any one of specific embodiments one, two, six and seven or mixtures as defined in any one of specific embodiments one to nine or of compositions according to specific embodiment ten in (i) preparations ready for use or consumption or (ii) semifinished products, used for staple or luxury foods, in particular sodium glutamate-reduced or -free preparations used in staple or luxury foods.

Specific embodiment twelve comprises a preparation comprising compounds as defined in any one of specific embodiments one, two, six and seven or mixtures as defined in any one of specific embodiments one to nine or compositions according to specific embodiment ten.

Specific embodiment thirteen comprises semifinished products comprising compounds as defined in any one of specific embodiments one, two, six and seven or mixtures as defined in any one of specific embodiments one to nine or compositions according to specific embodiment ten.

Specific embodiment fourteen comprises a method for producing, imparting, modifying and/or enhancing a flavor impression, wherein a compound as defined in any one of specific embodiments one, two, six, and seven or a mixture as defined in any one of specific embodiments one to nine or a composition as defined in specific embodiment ten or a preparation as in specific embodiment twelve or a semifinished product as in specific embodiment thirteen is added to a substance or composition in an effective flavoring amount.

The invention claimed is:

1. A method for imparting or enhancing an umami flavor to a material comprising adding to the material:
    (a) a compound or a mixture of compounds selected from the group consisting of:
        (1) 1-((1S,2S,5R)-2-isopropyl-5-methyl-cyclohexyl)-3-(3-methoxy-propyl)-urea,
        (2) 1-((1R,2R,5S)-2-isopropyl-5-methyl-cyclohexyl)-3-(3-methoxy-propyl)-urea,
        (3) 1-(3-hydroxy-propyl)-3-((1S,2S,5R)-2-isopropyl-5-methyl-cyclohexyl)-urea,
        (4) 1-(3-hydroxy-propyl)-3-((1R,2R,5S)-2-isopropyl-5-methyl-cyclohexyl)-urea,
        (5) 1-((1S,2S,5R)-2-isopropyl-5-methyl-cyclohexyl)-3-(2-methoxy-1-methyl-ethyl)-urea,
        (6) 1-((1R,2R,5S)-2-isopropyl-5-methyl-cyclohexyl)-3-(2-methoxy-1-methyl-ethyl)-urea,
        (7) 3-[3-((1S,2S,5R)-2-isopropyl-5-methyl-cyclohexyl)-ureido]-butyric acid ethyl ester,
        (8) 3-[3-((1R,2R,5S)-2-isopropyl-5-methyl-cyclohexyl)-ureido]-butyric acid ethyl ester,
        (9) (3-methoxy-propyl)-carbamic acid (1S,2S,5R)-2-isopropyl-5-methyl-cyclohexyl ester,
        (10) (3-methoxy-propyl)-carbamic acid (1R,2R,5S)-2-isopropyl-5-methyl-cyclohexyl ester,
        (11) 4-((1S,2S,5R)-2-isopropyl-5-methyl-cyclohexyloxycarbonylamino)-butyric acid ethyl ester, and
        (12) 4-((1R,2R,5S)-2-isopropyl-5-methyl-cyclohexyloxycarbonylamino)-butyric acid ethyl ester,
thereby imparting or enhancing an umami flavor.

2. The method of claim 1, wherein the method comprises adding a mixture of compounds of group (a) to the material.

3. The method of claim 2, wherein the mixture comprises enantiomers or epimer pairs.

4. The method of claim 1, further comprising adding to the material:

(b) one or more compounds selected from the group consisting of compounds of formulae (II), (ent-II), (III), (ent-III), (IV), and (ent-IV):

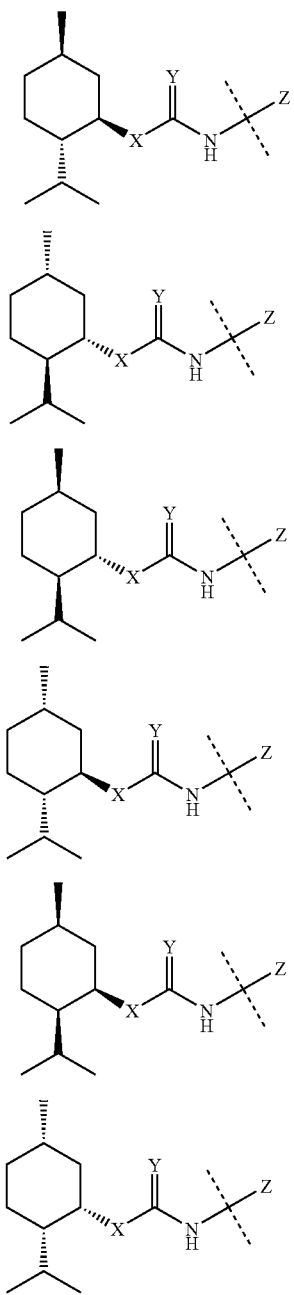

wherein the dashed line respectively marks the bond which links the organic residue Z to the neighboring nitrogen atom in formula (II), (ent-II), (III), (ent-III), (IV), and (ent-IV), wherein the following apply independently of one another in formulae (II), (ent-II), (III), (ent-III), (IV), and (ent-IV):

X=NH or O;

Y=O, S or NR¹, where R¹ denotes hydrogen, methyl, ethyl, propyl or isopropyl; and Z=organic residue having at most 15 C atoms, and wherein the weight ratio of (a) to (b) is at least 60:40.

5. The method of claim 4, wherein weight ratio of (a) to (b) is at least 90:10.

6. The method of claim 5, wherein weight ratio of (a) to (b) is at least 95:5.

7. A composition comprising:

(a) a compound or a mixture of compounds in an amount sufficient to impart or enhance an umami flavor selected from the group consisting of:

(1) 1-((1S,2S,5R)-2-isopropyl-5-methyl-cyclohexyl)-3-(3-methoxy-propyl)-urea, (2) 1-((1R,2R,5S)-2-isopropyl-5-methyl-cyclohexyl)-3-(3-methoxy-propyl)-urea, (3) 1-(3-hydroxy-propyl)-3-((1S,2S,5R)-2-isopropyl-5-methyl-cyclohexyl)-urea, (4) 1-(3-hydroxy-propyl)-3-((1R,2R,5S)-2-isopropyl-5-methyl-cyclohexyl)-urea, (5) 1-((1S,2S,5R)-2-isopropyl-5-methyl-cyclohexyl)-3-(2-methoxy-1-methyl-ethyl)-urea, (6) 1-((1R,2R,5S)-2-isopropyl-5-methyl-cyclohexyl)-3-(2-methoxy-1-methyl-ethyl)-urea, (7) 3-[3-((1S,2S,5R)-2-isopropyl-5-methyl-cyclohexyl)-ureido]-butyric acid ethyl ester, (8) 3-[3-((1R,2R,5S)-2-isopropyl-5-methyl-cyclohexyl)-ureido]-butyric acid ethyl ester, (9) (3-methoxy-propyl)-carbamic acid (1S,2S,5R)-2-isopropyl-5-methyl-cyclohexyl ester,

(10) (3-methoxy-propyl)-carbamic acid (1R,2R,5S)-2-isopropyl-5-methyl-cyclohexyl ester,

(11) 4-((1S,2S,5R)-2-isopropyl-5-methyl-cyclohexyloxycarbonylamino)-butyric acid ethyl ester, and

(12) 4-((1R,2R,5S)-2-isopropyl-5-methyl-cyclohexyloxycarbonylamino)-butyric acid ethyl ester.

8. The composition of claim 7 comprising a mixture of compounds of group (a).

9. The composition of claim 8, wherein the mixture comprises enantiomers or epimer pairs.

10. The composition of claim 7 further comprising:

(b) one or more compounds selected from the group consisting of compounds of formulae (II), (ent-II), (III), (ent-III), (IV), and (ent-IV):

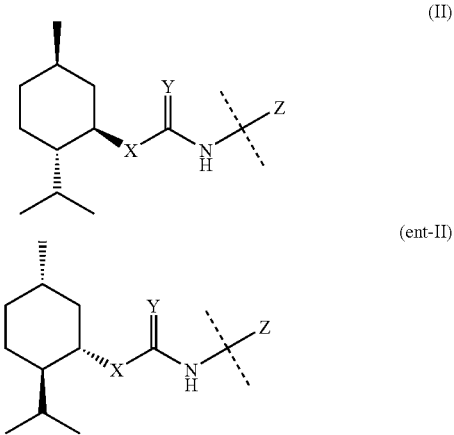

-continued

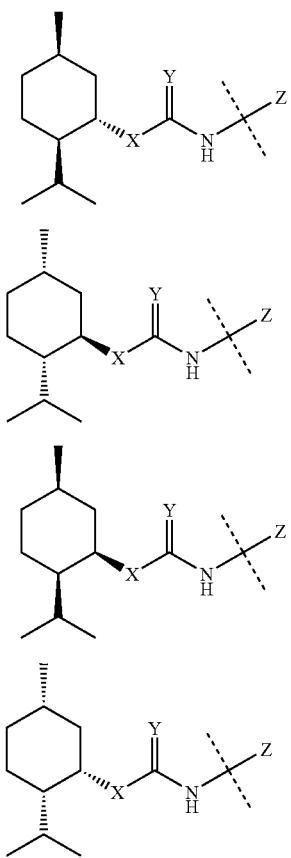

(III)

(ent-III)

(IV)

(ent-IV)

wherein the dashed line respectively marks the bond which links the organic residue Z to the neighboring nitrogen atom in formula (II), (ent-II), (III), (ent-III), (IV), and (ent-IV):

wherein the following apply independently of one another in the formulae (II), (ent-II), (III), (ent-III), (IV), and (ent-W):

X=NH or O;

Y=O, S or NR$^1$, where R$^1$ denotes hydrogen, methyl, ethyl, propyl or isopropyl; and Z=organic residue consisting of carbon and hydrogen atoms and optionally oxygen atoms, Wherein the sum of the number of carbon and oxygen atoms is at most 15 and the number of oxygen atoms is at most 4, and the atom by which the organic residue Z is bound to the neighboring nitrogen in formula (I) or (ent-I) is carbon, with the condition that the organic residue Z does not contain a C—C double or triple bond, contains at most one aromatic ring that may have a C—C double bond, and is not a group —C(=Y$^2$)—R$^2$ in which Y$^2$ has any of the meanings specified above for Y and R$^2$ is any organic residue, Z is not —C(R$^5$)(R$^6$)—C(=O)OR$^4$, where R$^4$ denotes H, methyl, ethyl, propyl, iso-propyl, butyl, iso-butyl or tert-butyl and R5 and R6 independently of one another denote H or an organic residue, if X=NH and Y=O, then Z is not neomenthyl, 2-methylcyclohexyl or phenyl, and if X=NH and Y=S, then Z is not neomenthyl or phenyl, and if X=O and Y=O, then Z does not denote ethyl, hydroxyethyl, 1-phenylethyl, 2-phenylethyl, 2-hydroxy-1-methyl-2-phenylethyl, isopropyl, 2-hydroxy-1-methylethyl, cyclohexyl, 4-hydroxyphenyl, 2-hydroxy-5-methylphenyl or 2,4,7-trioxa-3,3,8-trimethylbicyclo [3.3.0]octan-6-ylmethyl, and wherein the weight ratio of (a) to (b) is at least 60:40.

11. The composition of claim 10, wherein weight ratio of (a) to (b) is at least 90:10.

12. The composition of claim 11, wherein weight ratio of (a) to (b) is at least 95:5.

13. The composition of claim 7 further comprising one or more constituents suitable for consumption.

14. Food comprising a composition of claim 7.

15. A preparation ready for use or consumption comprising a composition of claim 7.

16. A semi-finished food product comprising a composition of claim 7.

17. The food of claim 14, wherein the food is sodium glutamate-reduced or sodium glutamate-free, wherein said sodium glutamate-reduced food contains at least 5 to <100 wt. % less sodium glutamate content than the sodium glutamate content of a comparable conventional preparation.

* * * * *

UNITED STATES PATENT AND TRADEMARK OFFICE
CERTIFICATE OF CORRECTION

| | | |
|---|---|---|
| PATENT NO. | : 8,852,664 B2 | Page 1 of 1 |
| APPLICATION NO. | : 12/482210 | |
| DATED | : October 7, 2014 | |
| INVENTOR(S) | : Jakob Peter Ley et al. | |

It is certified that error appears in the above-identified patent and that said Letters Patent is hereby corrected as shown below:

In the Claims:

At column 71, claim number 10, line number 43, change as follows:

(IV), and (*ent*-IV):

Signed and Sealed this
Twenty-fourth Day of February, 2015

Michelle K. Lee
*Deputy Director of the United States Patent and Trademark Office*